US012576018B2

(12) United States Patent
Pesaro et al.

(10) Patent No.: US 12,576,018 B2
(45) Date of Patent: **\*Mar. 17, 2026**

(54) ACTIVE AGENTS FOR SKIN AND HAIR CARE WITH SENSORY MODIFYING PROPERTIES

(71) Applicant: SYMRISE AG, Holzminden (DE)

(72) Inventors: Manuel Pesaro, Vernier (CH); Sabine Lange, Holzminden (DE); Ricarda Kräling, Holzminden (DE); Christin Koch, Detmold (DE)

(73) Assignee: SYMRISE AG, Holzminden (DE)

( \* ) Notice: Subject to any disclaimer, the term of this patent is extended or adjusted under 35 U.S.C. 154(b) by 759 days.

This patent is subject to a terminal disclaimer.

(21) Appl. No.: 17/428,350

(22) PCT Filed: Feb. 4, 2019

(86) PCT No.: PCT/EP2019/052578
§ 371 (c)(1),
(2) Date: Aug. 4, 2021

(87) PCT Pub. No.: WO2020/160742
PCT Pub. Date: Aug. 13, 2020

(65) Prior Publication Data
US 2022/0096347 A1 Mar. 31, 2022

(51) Int. Cl.
| | |
|---|---|
| *A61K 8/37* | (2006.01) |
| *A61K 8/92* | (2006.01) |
| *A61Q 5/00* | (2006.01) |
| *A61Q 5/02* | (2006.01) |

(52) U.S. Cl.
CPC ................ *A61K 8/37* (2013.01); *A61K 8/922* (2013.01); *A61Q 5/006* (2013.01); *A61Q 5/02* (2013.01); *A61K 2800/524* (2013.01)

(58) Field of Classification Search
None
See application file for complete search history.

(56) References Cited

U.S. PATENT DOCUMENTS

| | | | | |
|---|---|---|---|---|
| 2010/0034761 A1\* | 2/2010 | Fenyvesi | .............. | C11D 7/5022 424/59 |
| 2010/0215775 A1\* | 8/2010 | Schmaus | .............. | A61K 9/0014 514/588 |

FOREIGN PATENT DOCUMENTS

| | | |
|---|---|---|
| CN | 103561714 A | 2/2014 |
| CN | 109157505 A | 1/2019 |
| EP | 2548448 A1 | 1/2013 |
| EP | 3920896 A1 | 2/2019 |
| JP | H09110648 A | 4/1997 |
| JP | 2002155295 A | 5/2002 |
| JP | 2011046747 A | 3/2011 |
| JP | 2018123129 A | 8/2018 |
| WO | 2011101239 A2 | 8/2011 |
| WO | 2018012021 A1 | 1/2018 |

OTHER PUBLICATIONS

Chinese Office Action issued on Jan. 12, 2023, for corresponding Chinese Application No. 201980093542.9.
International Search Report and Written Opinion issued on Oct. 21, 2019 for corresponding PCT Application No. PCT/EP2019/052578.
Database GNPD; Mintel; "Children Shampoo," 2017; pp. 1-3 XP055627429.
European Office Action issued on Jun. 26, 2024 for corresponding European Application No. 19 703 291.5.
A. Thiemann et al.; "Wetting Agents—Their Concentration-Dependent Effects on the Energy Demand in the Formation of Stable Emulsions," SOFW Journal, vol. 141, No. 3, 2015, pp. 10-16 XP055743220.
Chinese Office Action issued on Apr. 2, 2025 for corresponding Chinese Application No. 202310577592.2.

\* cited by examiner

*Primary Examiner* — Jennifer A Berrios
(74) *Attorney, Agent, or Firm* — POLSINELLI PC

(57) ABSTRACT

The present invention primarily relates to the use of a fatty acid ester or of a mixture of two or more fatty acid esters or of a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, for modifying the sensory properties of a skin care product. The present invention further relates to methods for modifying the sensory properties of a skin care product as well as to methods for manufacturing a skin care product and to particular skin care products.

18 Claims, 6 Drawing Sheets

ACTIVE AGENTS FOR SKIN AND HAIR CARE WITH SENSORY MODIFYING PROPERTIES

CROSS-REFERENCE TO RELATED APPLICATIONS

This application is a national stage application (under 35 U.S.C. § 371) of PCT/EP2019/052578, filed Feb. 4, 2019, which is incorporated herein by reference in its entirety.

The present invention primarily relates to the use of a fatty acid ester or of a mixture as defined herein for modifying the sensory properties of a skin care product. The present invention further relates to methods for modifying the sensory properties of a skin care product as well as to methods for manufacturing a skin care product and to particular skin care products.

Further aspects of the present invention will arise from the description below, in particular from the examples, as well as from the attached patent claims.

*Malassezia* is a genus of fungi and is naturally found on the skin surfaces of many animals, including humans. As the fungus requires fat to grow, it is most common in areas with many sebaceous glands, i.e. on the scalp, face, and upper part of the body. However, when the fungus grows too rapidly, the natural renewal of cells is disturbed and, for example, dandruff appears on the scalp along with an itching sensation.

It is also well known that substances for care of the skin, particularly the scalp, are used in particular formulations such as, for example, shampoos or gels. Positive sensory properties of an active agent, such as e.g. of a topical antifungal agent against dandruff, in these formulations are highly desirable, since they facilitate the manufacture of the formulations and may be experienced in a positive way by the end user. Such positive sensory properties of an active agent are e.g. the ability to improve the foam formation on the skin or the skin sensation of the formulation.

None of the typically used topical antifungal agents, such as e.g. climbazole, zinc pyrithione and piroctone olamine, display any such positive sensory properties in skin care formulations.

In DE 42 37 367 A1 fatty acid esters are described as antimycotic agents. These esters are preferably selected from the group of hexyl laurate, isopropyl stearate, glyceryl monolaurate, caprylic acid tryglyceride and capric acid tryglyceride. No sensory properties of the active agents are disclosed.

DE 42 34 188 A1 relates to ethoxylated and propoxylated organic compounds as antimycotic agents in cosmetics. No sensory properties of the active agents are disclosed.

DE 10 2004 046 603 A1 describes substance mixtures comprising fatty acid esters of polyols and salts of short chain fatty acids to counteract microorganisms. Again, DE 10 2004 046 603 A1 does not disclose any sensory properties of the active agents.

SU 1286204 A1 discloses the use of a mixture of mono-(50-60%), di- (30-35%) and triesters (10-15%) of glycerol and undecylenic acid to give antimicrobial properties to a cosmetic base. It also discloses that the mixture combines well with other ingredients of cosmetic products and shampoos.

DE 33 14 786 A1 discloses a mixture with antimycotic activity comprising mono and/or di-10-undecylenic acid glyceryl esters. The mixtures are used in the treatment of nasal cavity mycosis and onychomycosis. It does not disclose any sensory properties of the active agents.

In WO 2006/054110 A2, esters of 1,2,3-propanetriol with one or more Cl 1 to C24 fatty acids are described, wherein at least one fatty acid has at least one double bond. The application field for these substances is the treatment of chronic inflammatory disorders.

WO 2007/095262 A2 discloses 1,3-propanediol esters for the purpose of dissolving botanical extracts, fragrance concentrates and oils.

It was thus an object of the present invention to provide skin care agents that impart positive sensory properties to a skin care formulation. Moreover, it was an object of the present invention to provide certain skin care formulations, such as e.g. (anti-dandruff) shampoos, with particularly positive sensory properties.

BRIEF DESCRIPTION OF THE DRAWINGS

Implementation of the present technology is described, by way of the example only, with reference to the attached figure, wherein.

Figure 1:
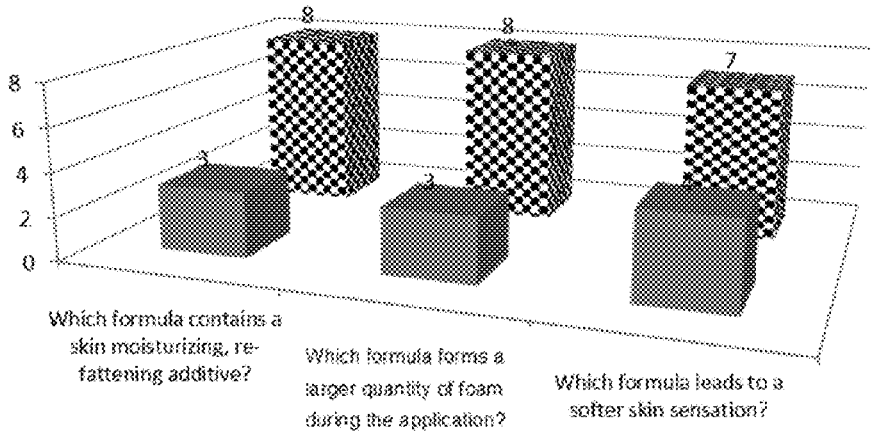
FIG. 1 illustrates the results of a sensory evaluation comparing a placebo shampoo formulation and a shampoo formulation containing 1 wt.-% 3-hydroxypropyl undecylenate, including assessments of moisturization/re-fattening, foam formation, and post-rinse skin softness.

The various aspects of the disclosure are not limited to the results, arrangements, and representations shown in the drawings.

According to a first aspect of the present invention, the stated object is achieved by the use of a fatty acid ester or of a mixture of two or more fatty acid esters or of a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, for modifying the sensory properties of a skin care product.

Within the framework of the present text, a modification of the sensory properties of a skin care product, preferably of a scalp care product, preferably relates to a modification of one, more or all characteristics selected from the group consisting of ability of foam formation on the skin and skin sensation of a skin care product, preferably of a scalp care product. The skin sensation of a skin care product preferably relates to e.g. a sensation of (increased) smoothness, re-fattening properties, moisturizing properties, film forming properties, speed of absorption and/or (decreased) stickiness and/or soapiness of a skin care product. Moreover, it preferably relates to the skin sensation a skin care product imparts to the skin of a user of a skin care product e.g. that the skin, preferably the scalp, of said user feels well-cared for, re-fattened, moisturized, smoother, (more) pleasant and/or less itchy. Preferred and particularly advantageous modifications of the sensory properties of a skin care product according to the present invention will be described below.

Caprylate refers to an ester of caprylic acid (CAS Registry Number of caprylic acid: 124-07-2; also known as octanoic acid) and undecylenate refers to an ester of 10-undecylenic acid (CAS Registry Number of 10-undecylenic acid: 112-38-9; also known as 10-undecenoic acid).

3-Hydroxypropyl caprylate refers to the monoester of the alcohol 1,3-propanediol (CAS Registry Number: 504-63-2) with caprylic acid and 3-hydroxypropyl undecylenate refers to the monoester of the alcohol 1,3-propanediol with 10-undecylenic acid. Glyceryl monocaprylate refers to a monoester of (mono)glycerol (CAS Registry Number: 56-81-5; also known as 1,2,3-propanetriol) with caprylic acid and glyceryl monoundecylenate refers to a monoester of (mono)glycerol with undecylenic acid.

A preferred embodiment of the present invention relates to the use of a fatty acid ester or of a mixture of two or more fatty acid esters or of a mixture comprising one or more fatty acid esters, wherein the fatty acid ester or one, two or three, preferably all, of the fatty acid ester(s) is/are selected from the group consisting of 3-hydroxypropyl caprylate, glyceryl monocaprylate and 3-hydroxypropyl undecylenate, for modifying the sensory properties of a skin care product.

Another preferred embodiment of the invention relates to the use of a fatty acid ester or of a mixture of two or more fatty acid esters or of a mixture comprising one or more fatty acid esters, wherein the fatty acid ester or one, two or three, preferably all, of the fatty acid ester(s) is/are selected from the group consisting of 3-hydroxypropyl caprylate, 3-hydroxypropyl undecylenate and glyceryl monoundecylenate, for modifying the sensory properties of a skin care product.

A particularly preferred embodiment of the invention relates to the use of a fatty acid ester or of mixture of two or more fatty acid esters or of a mixture comprising one or more fatty acid esters, wherein the fatty acid ester or one or two, preferably all, of the fatty acid ester(s) is/are selected from the group consisting of 3-hydroxypropyl caprylate and 3-hydroxypropyl undecylenate, for modifying the sensory properties of a skin care product.

A preferred embodiment of the invention relates to the use of 3-hydroxypropyl caprylate or of glyceryl monocaprylate or of 3-hydroxypropyl undecylenate or of glyceryl monoundecylenate or of a mixture comprising 3-hydroxypropyl caprylate or comprising glyceryl monocaprylate or comprising 3-hydroxypropyl undecylenate or comprising glyceryl monoundecylenate for modifying the sensory properties of a skin care product.

Another preferred embodiment of the invention relates to the use of a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate, or to the use of a mixture comprising 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate for modifying the sensory properties of a skin care product.

Another preferred embodiment of the invention relates to the use of a mixture of 3-hydroxypropyl caprylate, glyceryl monocaprylate and 3-hydroxypropyl undecylenate, or to the use of a mixture comprising 3-hydroxypropyl caprylate, glyceryl monocaprylate and 3-hydroxypropyl undecylenate for modifying the sensory properties of a skin care product.

Another preferred embodiment of the invention relates to the use of a mixture of 3-hydroxypropyl caprylate, glyceryl monocaprylate, 3-hydroxypropyl undecylenate and glyceryl monoundecylenate, or to the use of a mixture comprising 3-hydroxypropyl caprylate, glyceryl monocaprylate, 3-hydroxypropyl undecylenate and glyceryl monoundecylenate for modifying the sensory properties of a skin care product.

Another preferred embodiment relates to the use of a fatty acid ester or mixture as defined herein, wherein the total amount of said fatty acid or mixture comprised in the skin care product as defined herein is from 0.02 to 5 wt.-%, more preferably from 0.05 to 2 wt.-%, most preferably from 0.1 to 1 wt.-%, relative to the total weight of said skin care product.

Another preferred embodiment of the present invention relates to the use of a mixture as defined herein, wherein the mixture comprises one or more additional active agent(s), preferably one or more anti-itching agent(s), more preferably one or more active agent(s) selected from the group consisting of laureth-9, crisaborol, trideceth-9, PEG-5 isononanoate, 4-t-butylcyclohexanol, hydroxyphenyl propamidobenzoic acid, avananthramides, polyphenols from oats, hydrocortisone and urea.

A preferred alternative embodiment relates to the use of a fatty acid ester as defined herein, wherein the fatty acid ester is used in combination with one or more additional active agent(s), preferably with one or more anti-itching agent(s), more preferably with one or more active agent(s) selected from the group consisting of laureth-9, crisaborol, trideceth-9, PEG-5 isononanoate, 4-t-butylcyclohexanol, hydroxyphenyl propamidobenzoic acid, avananthramides, polyphenols from oats, hydrocortisone and urea.

It was surprisingly found that the fatty acid esters or mixtures as defined herein do not only show excellent antimycotic activity against dandruff-causing *Malassezia* spp., but also are able to significantly alter the sensory properties (as defined above) of skin care products such as e.g. (anti-dandruff) shampoos.

Thus, a preferred embodiment of the invention relates to the use as defined herein, wherein the skin care product is a product selected from the group consisting of leave-on skin care product, preferably oil in water emulsion or aqueous formulation or aqueous and/or ethanolic and/or glycolic-based formulations or water in oil emulsion, and rinse-off skin care product, preferably shampoo, more preferably anti-dandruff shampoo, surfactant-based cleansing formulation, more preferably micellar water, or shower gel.

Preferably, the modified skin care product is a leave-on skin care product, preferably an oil in water emulsion or a water in oil emulsion.

Another preferred embodiment of the invention relates to the use as defined herein, wherein the modification of the sensory properties is an improvement of the foam formation on the skin or of the skin sensation of the skin care product.

Within the framework of the present text, the skin sensation of a skin care product preferably relates to e.g. a sensation of (increased) smoothness, re-fattening properties, moisturizing properties, film forming properties, speed of absorption and/or (decreased) stickiness and/or soapiness of a skin care product. Moreover, it preferably relates to the skin sensation a skin care product imparts to the skin of a user of a skin care product e.g. that the skin, preferably the scalp, of said user feels well-cared for, re-fattened, moisturized, smoother, (more) pleasant and/or less itchy. Preferred and particularly advantageous modifications of the sensory properties of a skin care product according to the present invention will be described below.

Particularly rinse-off skin care products are usually used in a way that the consumer mixes the product with water during use and creates the desired amount of foam on the skin or scalp by rubbing the water/skin care product mixture on the skin or scalp surface. It is thus desirable for the consumer when the foam formation takes place fast and without much effort. During the studies underlying the present invention, it was surprisingly found that the addition of the fatty acid esters or mixtures as defined herein to skin care products, particularly rinse-off skin care products such as (anti-dandruff) shampoos or shower gels, significantly facilitates and improves the foam formation on the skin. The level of foam formation on the skin is determined as described in the examples further below.

Advantageously, the use of a fatty acid ester or mixture as defined herein (also) improves the skin sensation of the skin care product, i.e. it makes the skin care product for example feel (more) smooth, skin and/or hair caring, re-fattening, moist/moisturizing, film forming, fast absorbing and/or less sticky and/or soapy. Moreover, the use of a fatty acid ester or mixture for modifying the sensory properties of a skin care product as defined herein leads to a skin care product that it makes the skin, preferably the scalp, of a user of said product feel well-cared for, re-fattened, moisturized, smoother, (more) pleasant and/or less itchy.

Thus, another particularly preferred embodiment of the invention relates to the use as defined herein, wherein the improvement of the skin sensation of the skin care product is an increase in the sensation of smoothness, skin and/or hair caring, re-fattening, moisturizing and/or film formation abilities and/or in the speed of absorption of the skin care product and/or is a decrease in the sensation of stickiness and/or soapiness of the skin care product. Said sensory properties of the skin care product are determined as described in the examples further below.

Another particularly preferred embodiment of the invention relates to the use as defined herein, wherein the improvement of the skin sensation of the skin care product is that it makes the skin, preferably the scalp, of a user of said product feel well-cared for, re-fattened, moisturized, smoother, (more) pleasant and/or less itchy.

Another preferred embodiment of the invention relates to the use as defined herein, wherein the fatty acid ester or mixture as defined herein are further used to avoid dandruff and/or to reduce the amount of dandruff on human skin, preferably on human scalp.

Within the framework of the present text, the term "avoiding dandruff on human skin, preferably on human scalp" relates to a preventive measure where the first occurrence or reoccurrence of dandruff on a defined area of human skin, preferably of human scalp, is avoided by applying the fatty acid esters or mixtures as defined herein once or repeatedly to said defined area of human skin. As a result, no dandruff is visible on said defined area of the human skin when inspected by naked human eye.

Within the framework of the present text, the term "reducing the amount of dandruff on human skin, preferably on human scalp" relates to a measure where the total amount of dandruff on a defined area of human skin, preferably of human scalp, as observed by naked human eye is reduced by more than 10, 20, 30, 40 50, 60, 70, 80 or 90% after one-off or repeated treatment of said defined area with the fatty acid esters or mixtures as defined herein.

Another aspect of the present invention relates to a method for modifying the sensory properties of a skin care product comprising or consisting of the following steps:
(i) providing the ingredients of a skin care product or a skin care product (apart from the substance(s) provided in step (ii)),
(ii) providing a fatty acid ester or a mixture of two or more fatty acid esters or a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate,
(iii) mixing the components of steps (i) and (ii).

A preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, glyceryl monocaprylate and 3-hydroxypropyl undecylenate.

Another preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, 3-hydroxypropyl undecylenate and glyceryl monoundecylenate.

Another preferred embodiment of the present invention relates to a method as defined herein, wherein the fatty acid ester or one or two, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester provided in step (ii) is 3-hydroxypropyl caprylate or glyceryl monocaprylate or 3-hydroxypropyl undecylenate or glyceryl monoundecylenate.

Another preferred embodiment of the present invention relates to a method as defined herein, wherein the mixture comprising one or more fatty acid esters provided in step (ii) comprises 3-hydroxypropyl caprylate or glyceryl monocaprylate or 3-hydroxypropyl undecylenate or glyceryl monoundecylenate.

Another preferred embodiment of the present invention relates to a method as defined herein, wherein the mixture of two or more fatty acid esters provided in step (ii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a method as defined herein, wherein the mixture comprising one or more fatty acid esters provided in step (ii) comprises 3-hydroxypropyl caprylate and 3-hydroxypropyl undecylenate, or glyceryl monocaprylate and 3-hydroxypro-pyl undecylenate, or 3-hydroxypropyl caprylate and glyceryl monoundecylenate, or glyceryl monocaprylate and glyceryl monoundecylenate, or 3-hydroxypropyl caprylate and glyc-eryl monocaprylate.

Another preferred embodiment of the present invention relates to a method as defined herein, wherein the mixture of two or more fatty acid esters provided in step (ii) is a mixture of 3-hydroxypropyl caprylate, glyceryl monocaprylate and 3-hydroxypropyl undecylenate.

Another preferred embodiment of the present invention relates to a method as defined herein, wherein the mixture comprising one or more fatty acid esters provided in step (ii) comprises 3-hydroxypropyl caprylate, glyceryl monocapry-late and 3-hydroxypropyl undecylenate.

Another preferred embodiment of the present invention relates to a method as defined herein, wherein the mixture of two or more fatty acid esters provided in step (ii) is a mixture of 3-hydroxypropyl caprylate, glyceryl monocaprylate, 3-hydroxypropyl undecylenate and glyceryl monoun-decylenate.

Another preferred embodiment of the present invention relates to a method as defined herein, wherein the mixture comprising one or more fatty acid esters provided in step (ii) comprises 3-hydroxypropyl caprylate, glyceryl monocapry-late, 3-hydroxypropyl undecylenate and glyceryl monoun-decylenate.

Another preferred embodiment of the present invention relates to a method as defined herein, wherein the total amount of the fatty acid ester or the mixture of two or more fatty acid esters or the mixture comprising one or more fatty acid esters provided in step (ii) is from 0.02 to 5 wt.-%, more preferably from 0.05 to 2 wt.-%, most preferably from 0.1 to 1 wt.-%, relative to the total weight of the skin care product obtained in step (iii).

Step (i) of the method as described herein may take place before step (ii) or step (i) of the method as described herein may take place after step (ii).

In the method as defined herein, the ingredients of a skin care product (apart from the substances provided in step (ii)) provided in step (i) may be provided separately or (partly) pre-mixed. The same applies to the fatty acid esters provided in step (ii), i.e. the fatty acid esters of the mixture of two or more fatty acid esters or the fatty acid ester(s) and other ingredient(s) of the mixture comprising one or more fatty acid esters may be provided separately (so that they only form the respective mixture after step (iii)) or (partly) pre-mixed.

The fatty acid ester or mixtures as described herein provided in step (ii) preferably is/are provided in an amount that is sufficient to modify the sensory properties (as defined above) of the final skin care product (i.e. product of step (iii)).

Another embodiment relates to a method as defined herein, wherein one or more additional active agent(s), preferably one or more anti-itching agent(s), more prefer-ably one or more active agent(s) selected from the group consisting of laureth-9, crisaborol, trideceth-9, PEG-5 isononanoate, 4-t-butylcyclohexanol, hydroxyphenyl pro-pamidobenzoic acid, avananthramides, polyphenols from oats, hydrocortisone and urea, are provided in addition to the components provided in steps (i) and (ii) and wherein said additional active agent(s) are mixed with the components of steps (i) and (ii) in step (iii) or are mixed with the product resulting from step (iii).

A preferred embodiment of the present invention relates to a method as defined herein, wherein the skin care product is a product selected from the group consisting of leave-on skin care product, preferably oil in water emulsion or aqueous formulation or aqueous and/or ethanolic and/or glycolic-based formulations or water in oil emulsion, and rinse-off skin care product, preferably shampoo, more pref-erably anti-dandruff shampoo, surfactant-based cleansing formulation, more preferably micellar water, or shower gel.

Preferably, the skin care product whose sensory properties are modified in a method according to the invention is a leave-on skin care product, preferably oil in water emulsion or water in oil emulsion.

Another preferred embodiment relates to a method as defined herein, wherein the modification of the sensory properties of the skin care product is an improvement of the foam formation on the skin or of the skin sensation of the skin care product (as defined above).

What has been stated above with regard to the improve-ment of the foam formation on the skin or of the skin sensation of the skin care product in terms of the use as defined herein applies mutatis mutandis to the (preferred) embodiment(s) of the method as defined herein.

Another preferred embodiment relates to a method as defined herein, wherein the skin care product is a shampoo and the component(s) in step (ii) is/are provided in an amount that the resulting product is an anti-dandruff sham-poo, i.e. displays antimycotic properties.

Another aspect of the present invention relates to a method for manufacturing a product selected from the group consisting of leave-on skin care product, preferably oil in water emulsion or aqueous formulation or aqueous and/or ethanolic and/or glycolic-based formulations or water in oil emulsion, and rinse-off skin care product, preferably sham-poo, more preferably anti-dandruff shampoo, surfactant-based cleansing formulation, more preferably micellar water, or shower gel, comprising or consisting of the fol-lowing steps:

(i) providing the ingredients of a leave-on or rinse-off skin care product or a leave-on or rinse-off skin care product (apart from the substance(s) provided in step (ii)), (ii) providing a fatty acid ester or a mixture of two or more fatty acid esters or a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, (iii) mixing the components of steps (i) and (ii).

A preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, glyceryl monocaprylate and 3-hydroxypropyl undecylenate.

Another preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, 3-hydroxypropyl undecylenate and glyceryl monoundecylenate.

Another preferred embodiment of the present invention relates to a method as defined herein, wherein the fatty acid ester or one or two, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester provided in step (ii) is 3-hydroxypropyl caprylate or glyceryl monocaprylate or 3-hydroxypropyl undecylenate or glyceryl monoundecylenate.

Another preferred embodiment of the present invention relates to a method as defined herein, wherein the mixture comprising one or more fatty acid esters provided in step (ii) comprises 3-hydroxypropyl caprylate or glyceryl mono-caprylate or 3-hydroxypropyl undecylenate or glyceryl monoundecylenate.

Another preferred embodiment of the present invention relates to a method as defined herein, wherein the mixture of two or more fatty acid esters provided in step (ii) is a mixture of 3-hydroxypropyl caprylate and 3-hydroxypropyl undecylenate, or of glyceryl monocaprylate and 3-hydroxy-propyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a method as defined herein, wherein the mixture comprising one or more fatty acid esters provided in step (ii) comprises 3-hydroxypropyl caprylate and 3-hydroxypropyl undecylenate, or glyceryl monocaprylate and 3-hydroxypro-pyl undecylenate, or 3-hydroxypropyl caprylate and glyceryl monoundecylenate, or glyceryl monocaprylate and glyceryl monoundecylenate, or 3-hydroxypropyl caprylate and glyc-eryl monocaprylate.

Another preferred embodiment of the present invention relates to a method as defined herein, wherein the mixture of two or more fatty acid esters provided in step (ii) is a mixture of 3-hydroxypropyl caprylate, glyceryl monocaprylate and 3-hydroxypropyl undecylenate.

Another preferred embodiment of the present invention relates to a method as defined herein, wherein the mixture comprising one or more fatty acid esters provided in step (ii) comprises 3-hydroxypropyl caprylate, glyceryl monocapry-late and 3-hydroxypropyl undecylenate.

Another preferred embodiment of the present invention relates to a method as defined herein, wherein the mixture of two or more fatty acid esters provided in step (ii) is a mixture of 3-hydroxypropyl caprylate, glyceryl monocaprylate, 3-hydroxypropyl undecylenate and glyceryl monoun-decylenate.

Another preferred embodiment of the present invention relates to a method as defined herein, wherein the mixture comprising one or more fatty acid esters provided in step (ii) comprises 3-hydroxypropyl caprylate, glyceryl monocapry-late, 3-hydroxypropyl undecylenate and glyceryl monoun-decylenate.

Another preferred embodiment of the present invention relates to a method as defined herein, wherein the total amount of the fatty acid ester or the mixture of two or more fatty acid esters or the mixture comprising one or more fatty acid esters provided in step (ii) is from 0.02 to 5 wt.-%, more preferably from 0.05 to 2 wt.-%, most preferably from 0.1 to 1 wt.-%, relative to the total weight of the skin care product obtained in step (iii).

Preferably, the present invention relates to a method for manufacturing a leave-on skin care product, preferably an oil in water emulsion or a water in oil emulsion.

Step (i) of the method as described herein may take place before step (ii) or step (i) of the method as described herein may take place after step (ii).

In the method as defined herein, the ingredients of a leave-on or rinse-off skin care product (apart from the substance(s) provided in step (ii)) provided in step (i) may be provided separately or (partly) pre-mixed. The same applies to the fatty acid esters provided in step (ii), i.e. the fatty acid esters of the mixture of two or more fatty acid esters or the fatty acid ester(s) and other ingredient(s) of the mixture comprising one or more fatty acid esters may be provided separately (so that they only form the respective mixture after step (iii)) or (partly) pre-mixed.

Another embodiment relates to a method as defined herein, wherein one or more additional active agent(s), preferably one or more anti-itching agent(s), more prefer-ably one or more active agent(s) selected from the group consisting of laureth-9, crisaborol, trideceth-9, PEG-5 isononanoate, 4-t-butylcyclohexanol, hydroxyphenyl pro-pamidobenzoic acid, avananthramides, polyphenols from oats, hydrocortisone and urea, are provided in addition to the components provided in steps (i) and (ii) and wherein said additional active agent(s) are mixed with the components of steps (i) and (ii) in step (iii) or are mixed with the product resulting from step (iii).

According to a preferred embodiment, the fatty acid ester or mixtures as described herein provided in step (ii) of the method as described herein is/are provided in an amount that is sufficient to modify the sensory properties (as defined above) of the final skin leave-on or rinse-off care product (product of step (iii)).

Advantageously, the fatty acid ester or mixtures as defined herein provided in step (ii) of the method according to the invention improve(s) the skin sensation of the skin care product, i.e. it makes the skin care product for example feel (more) smooth, skin and/or hair caring, re-fattening, moist/moisturizing, film forming, fast absorbing and/or less sticky and/or soapy. Moreover, the fatty acid ester or mixtures as defined herein provided in step (ii) lead(s) to a skin care product that makes the skin, preferably the scalp, of a user of said product feel well-cared for, re-fattened, moisturized, smoother, (more) pleasant and/or less itchy.

Another preferred embodiment relates to a method as defined herein, wherein the product is a shampoo and the component(s) in step (ii) is/are provided in an amount that the resulting product is an anti-dandruff shampoo, i.e. dis-plays antimycotic properties.

Another aspect of the present invention relates to a shampoo, preferably an anti-dandruff shampoo, preferably manufactured according to a method as defined herein, comprising or consisting of (i) water, (ii) one or more surfactant(s) selected from the group consisting of sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lau-royl sarcosinate, glycol distearate, coco-betaine, PPG-5-ceteth-20, coco-glucoside, diethylhexyl sodium sulfosuc-cinate, ammonium cocoyl isethionate, ammonium cocoyl sarcosinate, diethylhexyl sodium sulfosuccinate, coc-amide-MEA, PEG-7 glyceryl cocoate, glycol/distearate and sodium oleoyl sarcosinate, (iii) a fatty acid ester or a mixture of two or more fatty acid esters or a mixture comprising one or more fatty acid esters as defined herein, (iv) one or more fragrance(s), optionally (v) one or more plant oil(s) selected from the group consisting of *persea gratissima* (avocado) oil, *Olea europaea* (olive) oil, *prunus amygdalus dulcis* (sweet almond) oil, *Helianthus annuus* (sunflower) seed oil, *Simmondsia chinensis* (jojoba) seed oil, *mauritia flexuosa* fruit oil, calophyllum inophyllum seed oil and *Triticum vulgare* (wheat) germ oil, (vi) one or more preservative(s) selected from the group consisting of 2-phenoxyethanol, benzyl alcohol, dehydroacetic acid, methyl paraben, sorbic acid and benzoic acid, and (vii) one or more active ingredient(s) selected from the group consisting of 4-hydroxyacetophenone, 1,2-pentanediol, 1,2-hexanediol, 1,2-octanediol, 1,2-decanediol, caprylhydroxamic acid, sorbitan caprylate, ethylhexylglycerine, laureth-9, crisaborol, trideceth-9, PEG-5 isononanoate, 4-t-butylcyclohexanol, hydroxyphenyl propamidobenzoic acid, avananthramides, polyphenols from oats, hydrocortisone and urea.

According to a preferred embodiment, the shampoo according to the invention comprises said components in the following amounts:

(ii) 0.5 to 80 wt.-% of one or more surfactant(s), (iii) 0.02 to 5 wt.-%, more preferably 0.05 to 2 wt.-%, most preferably 0.1 to 1 wt.-% of fatty acid ester or a mixture of two or more fatty acid esters or a mixture comprising one or more fatty acid esters as defined herein, (iv) 0.05 to about 2 wt.-% of one or more fragrance(s), optionally (v) 0.01 to 20 wt.-%, preferably 0.1 to 10 wt.-%, of one or more plant oil(s), (vi) 0.01 to 1 wt.-%, preferably 0.1 to 1 wt.-% of one or more preservative(s), (vii) 0.01 to 5 wt.-%, preferably 0.1 to 3 wt.-%, of one or more active ingredient(s), whereby said amounts add up—together with water and optionally with any additional ingredients present—to 100 wt.-%.

A preferred embodiment of the present invention relates to a shampoo as defined herein, wherein the fatty acid ester or one, two or three, preferably all, of the fatty acid ester(s) of component (iii) is/are selected from the group consisting of 3-hydroxypropyl caprylate, glyceryl monocaprylate and 3-hydroxypropyl undecylenate.

Another preferred embodiment of the present invention relates to a shampoo as defined herein, wherein the fatty acid ester or one, two or three, preferably all, of the fatty acid ester(s) of component (iii) is/are selected from the group consisting of 3-hydroxypropyl caprylate, 3-hydroxypropyl undecylenate and glyceryl monoundecylenate.

Another preferred embodiment of the present invention relates to a shampoo as defined herein, wherein the fatty acid ester or one or two, preferably all, of the fatty acid ester(s) of component (iii) is/are selected from the group consisting of 3-hydroxypropyl caprylate and 3-hydroxypropyl undecylenate.

Another preferred embodiment of the present invention relates to a shampoo as defined herein, wherein the fatty acid ester of component (iii) is 3-hydroxypropyl caprylate or glyceryl monocaprylate or 3-hydroxypropyl undecylenate or glyceryl monoundecylenate.

Another preferred embodiment of the present invention relates to a shampoo as defined herein, wherein the mixture comprising one or more fatty acid esters of component (iii)

comprises 3-hydroxypropyl caprylate or glyceryl monocaprylate or 3-hydroxypropyl undecylenate or glyceryl monoundecylenate.

Another preferred embodiment of the present invention relates to a shampoo as defined herein, wherein the mixture of two or more fatty acid esters of component (iii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a shampoo as defined herein, wherein the mixture comprising one or more fatty acid esters of component (iii) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a shampoo as defined herein, wherein the mixture of two or more fatty acid esters of component (iii) is a mixture of 3-hydroxypropyl caprylate, glyceryl monocaprylate and 3-hydroxypropyl undecylenate.

Another preferred embodiment of the present invention relates to a shampoo as defined herein, wherein the mixture comprising one or more fatty acid esters of component (iii) comprises 3-hydroxypropyl caprylate, glyceryl monocaprylate and 3-hydroxypropyl undecylenate.

Another preferred embodiment of the present invention relates to a shampoo as defined herein, wherein the mixture of two or more fatty acid esters of component (iii) is a mixture of 3-hydroxypropyl caprylate, glyceryl monocaprylate, 3-hydroxypropyl undecylenate and glyceryl monoundecylenate.

Another preferred embodiment of the present invention relates to a shampoo as defined herein, wherein the mixture comprising one or more fatty acid esters of component (iii) comprises 3-hydroxypropyl caprylate, glyceryl monocaprylate, 3-hydroxypropyl undecylenate and glyceryl monoundecylenate.

Advantageously, the fatty acid ester or mixtures as defined herein in component (iii) of the shampoo according to the invention improve(s) the skin sensation of the shampoo, i.e. it makes the shampoo for example feel (more) smooth, skin and/or hair caring, re-fattening, moist/moisturizing, film forming, fast absorbing and/or less sticky and/or soapy. Moreover, the fatty acid ester or mixtures as defined herein in component (iii) of the shampoo according to the invention lead(s) to a shampoo that makes the skin, preferably the scalp, of a user of said shampoo feel well-cared for, re-fattened, moisturized, smoother, (more) pleasant and/or less itchy.

Another aspect of the present invention relates to a hair or body cream, preferably manufactured according to a method as defined herein, comprising or consisting of (i) water, (ii) one or more emulsifying agent(s) selected from the group consisting of PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer (polymeric emulsifier), ammonium acryloyldimethyltaurate/Beheneth-25 methacrylate crosspolymer (polymeric emulsifier), polyglyceryl-4 caprate, polyglyceryl-4 caprylate/caprate, cetyl PEG/PPG-10/1, dimethicone, polyglycer-yl-6 dioleate, polyglyceryl-2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate se, polyglyceryl-3 dicitrate/stearate and PEG-40 hydrogenated castor oil, (iii) one or more oil(s) body/bodies selected from the group consisting of caprylic capric triglycerides, mineral oil, *Simmondsia chinensis* (jojoba) seed oil, butyrospermum parkii (shea) butter, dicaprylyl ether, cyclomethicone, dimethicone, C12-15 alkyl benzoate, isopropyl palmitate, isopropyl myristate, octyldodecanol, cetearyl ethylhexanoate, cetearyl nonanoate, ethylhexyl isononanoate, propylene glycol dicaprylate/dicaprate, propylheptyl caprylate, decyl oleate, hexyl laurate, ethylhexyl stearate, triisononanoin, iso-adipate, stearyl heptanoate and stearyl caprylate, (iv) a fatty acid ester or a mixture of two or more fatty acid esters or a mixture comprising one or more fatty acid esters as defined in claim 1, (v) one or more fragrance(s), optionally (vi) one or more preservative(s) selected from the group consisting of 2-phenoxyethanol, benzyl alcohol, dehydroacetic acid, methyl paraben, sorbic acid and benzoic acid, and (vii) one or more active ingredient(s) selected from the group consisting of 4-hydroxyacetophenone, 1,2-pentanediol, 1,2-hexanediol, 1,2-octanediol, 1,2-decanediol, caprylhydroxamic acid, sorbitan caprylate, ethylhexylglycerine, laureth-9, crisaborol, trideceth-9, PEG-5 isononanoate, 4-t-butylcyclohexanol, hydroxyphenyl propamidobenzoic acid, avananthramides, polyphenols from oats, hydrocortisone and urea.

According to a preferred embodiment, the hair or body cream according to the invention comprises said components in the following amounts:

(ii) 0.1 to 5 wt.-% of one or more emulsifying agent(s), (iii) 2 to about 40 wt.-% of one or more oil body/bodies, (iv) 0.02 to 5 wt.-%, preferably 0.05 to 2 wt.-%, more preferably 0.1 to 1 wt.-% of a fatty acid ester or a mixture of two or more fatty acid esters or a mixture comprising one or more fatty acid esters as defined herein, (v) 0.05 to 2 wt.-% of one or more fragrance(s), optionally (vi) 0.01 to 1 wt.-%, preferably 0.1 to 1 wt.-%, of one or more preservative(s), (vii) 0.01 to 5 wt.-%, preferably 0.1 to 3 wt.-%, of one or more active ingredient(s), whereby said amounts add up—together with water and optionally with any additional ingredients present—to 100 wt.-%.

A preferred embodiment of the present invention relates to a hair or body cream as defined herein, wherein the fatty acid ester or one, two or three, preferably all, of the fatty acid ester(s) of component (iv) is/are selected from the group consisting of 3-hydroxypropyl caprylate, glyceryl monocaprylate and 3-hydroxypropyl undecylenate.

Another preferred embodiment of the present invention relates to a hair or body cream as defined herein, wherein the fatty acid ester or one, two or three, preferably all, of the fatty acid ester(s) of component (iv) is/are selected from the group consisting of 3-hydroxypropyl caprylate, 3-hydroxypropyl undecylenate and glyceryl monoundecylenate.

Another preferred embodiment of the present invention relates to a hair or body cream as defined herein, wherein the fatty acid ester or one or two, preferably all, of the fatty acid ester(s) of component (iv) is/are selected from the group consisting of 3-hydroxypropyl caprylate and 3-hydroxypropyl undecylenate.

Another preferred embodiment of the present invention relates to a hair or body cream as defined herein, wherein the fatty acid ester of component (iv) is 3-hydroxypropyl caprylate or glyceryl monocaprylate or 3-hydroxypropyl undecylenate or glyceryl monoundecylenate.

Another preferred embodiment of the present invention relates to a hair or body cream as defined herein, wherein the mixture comprising one or more fatty acid esters of component (iv) comprises 3-hydroxypropyl caprylate or glyceryl monocaprylate or 3-hydroxypropyl undecylenate or glyceryl monoundecylenate.

Another preferred embodiment of the present invention relates to a hair or body cream as defined herein, wherein the mixture of two or more fatty acid esters of component (iv) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a hair or body cream as defined herein, wherein the mixture comprising one or more fatty acid esters of component (iv) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a hair or body cream as defined herein, wherein the mixture of two or more fatty acid esters of component (iv) is a mixture of 3-hydroxypropyl caprylate, glyceryl monocaprylate and 3-hydroxypropyl undecylenate.

Another preferred embodiment of the present invention relates to a hair or body cream as defined herein, wherein the mixture comprising one or more fatty acid esters of component (iv) comprises 3-hydroxypropyl caprylate, glyceryl monocaprylate and 3-hydroxypropyl undecylenate.

Another preferred embodiment of the present invention relates to a hair or body cream as defined herein, wherein the mixture of two or more fatty acid esters of component (iv) is a mixture of 3-hydroxypropyl caprylate, glyceryl monocaprylate, 3-hydroxypropyl undecylenate and glyceryl monoundecylenate.

Another preferred embodiment of the present invention relates to a hair or body cream as defined herein, wherein the mixture comprising one or more fatty acid esters of component (iv) comprises 3-hydroxypropyl caprylate, glyceryl monocaprylate, 3-hydroxypropyl undecylenate and glyceryl monoundecylenate.

Advantageously, the fatty acid ester or mixtures as defined herein in component (iv) of the hair or body cream according to the invention improve(s) the skin sensation of the hair or body cream, i.e. it makes the hair or body cream for example feel (more) smooth, skin and/or hair caring, re-fattening, moist/moisturizing, film forming, fast absorbing and/or less sticky and/or soapy. Moreover, the fatty acid ester or mixtures as defined herein in component (iv) of the hair or body cream according to the invention lead(s) to a hair or body cream that makes the skin, preferably the scalp, of a user of said hair or body cream feel well-cared for, re-fattened, moisturized, smoother, (more) pleasant and/or less itchy.

(Preferred) embodiments of the use according to the invention correspond to or can be derived from the (preferred) embodiments of the methods or products according to the invention, which are explained above, or vice versa.

The invention will now be described in more detail hereinafter with references to the examples.

EXAMPLES

1.) Sensory Assessment on Skin of 3-Hydroxypropyl Undecylenate

To evaluate the influence of 3-hydroxypropyl undecylenate on skin sensation and foam formation, the active ingredient was incorporated at 1 wt.-% dosage into a hair and body shampoo according to table 1.

Formulation A: Without active (placebo)

Formulation B: With 1 wt.-% 3-hydroxypropyl undecylenate

TABLE 1

Hair and body shampoo formulation

| | INCI | Placebo A | B |
|---|---|---|---|
| A. | Sodium Laureth Sulfate, Lauryl Glycoside | 17.0 | 17.0 |
| | Citric Acid | 0.15 | 0.15 |
| | 1,2-Hexanediol, Caprylyl Glycol | 1.0 | 1.0 |
| | Disodium EDTA | 0.1 | 0.1 |
| | Sodium Chloride | 0.4 | 0.4 |
| B. | Water (Aqua) | 76.2 | 75.2 |
| C. | Potassium Sorbate | 0.15 | 0.15 |
| D. | Cocoamidopropyl Betaine | 5.0 | 5.0 |
| | 3-Hydroxypropyl Undecylenate | — | 1.0 |
| | SUM | 100.0 | |

Eleven subjects were asked to test the active containing formulation B versus placebo A without active according to the procedure described below (samples were coded as A and B as in Table 1).

Test Procedure to Evaluate the Skin Sensation of Hair and Body Shampoo (Leave-on)

Cleaning of the hands by using 1 ml of a standard shampoo and rinsing water

Drying of the hands by using a towel

Hair and body shampoo (100 µl) was applied by the test manager using an Eppendorf pipette (Placebo without active (A) on the right index finger, formulation with 1 wt.-% active (B) on the left index finger)

Rubbing of the formulations between thumb, index finger and middle finger of the right (A) or left (B) hand for 20 seconds Question to be answered by the subjects:

Which formulation (A or B) contains a skin moisturizing, re-fattening additive?

Evaluation of Foam Quality and Skin Sensation (Rinse-Off)

Cleaning of the hands by using 1 ml of a standard shampoo and rinsing water

Drying of the hands by using a towel

Hair and body shampoo with and without active (100 µl) was applied on the back of the hand by the test manager using an Eppendorf pipette (placebo without active (A) on the back of the left or right hand and formulation with 1 wt.-% active (B) on the back of the opposite hand, respectively)

Rub 3 times and distribute the test sample on the back of each hand 20 ml of water was rinsed about each back of the hands Rub for 15 seconds and evaluate the foam volume of each formulation Question to be answered by the subjects:

Which formula (A or B) forms a larger quantity of foam during the application?

Wash off the formulation with rinsing water for 1 minute

Pat the skin dry by using a towel

Evaluate the skin sensation after 5 minutes

Question to be answered by the subjects:

Which formula (A or B) leads to a softer skin sensation?

TABLE 2

Results of evaluation (voting of eleven subjects)

| | Number of applicants | |
|---|---|---|
| Questions | Formulation A | Formulation B |
| Which formula contains a skin moisturizing/ re-fattening additive? | 3 | 8 |
| Which formula forms a larger quantity of foam during the application? | 3 | 8 |
| Which formula leads to a softer skin sensation? | 4 | 7 |

It could be clearly demonstrated that the hair and body shampoo formulation containing 1 wt.-% of 3-hydroxypropyl undecylenate (formulation B) leads to a more moisturized, more re-fattened skin sensation versus a placebo formulation without active (formulation A). Eight of eleven applicants voted that formulation B leads to a higher foam volume. Furthermore, seven out of eleven applicants voted that 3-hydroxypropyl undecylenate containing formulation B leads to a softer skin sensation after the formulation was rinsed off (cf. FIG. 1 below, where formulation A is depicted in grey and formulation B is depicted in chequered).

2.) Sensory Assessment on Skin of 3-Hydroxypropyl Caprylate

To evaluate the influence on skin sensation of 3-hydroxypropyl caprylate, the active ingredient was incorporated at a 1 wt.-% dosage into a hair and body shampoo according to table 3.

24 untrained panelists were asked to test the active containing formulation B versus placebo A without active according to the procedure described below (samples were coded A and B as in Table 3).

Formulation A: Without active (placebo)

Formulation B: With 1 wt.-% 3-hydroxypropyl caprylate

TABLE 3

Hair and body shampoo formulation

| | | w/w % | |
|---|---|---|---|
| | INCI | Placebo A | B |
| A. | Sodium Laureth Sulfate, Lauryl Glycoside | 17.0 | 17.0 |
| | Citric Acid | 0.15 | 0.15 |
| | 1,2-Hexanediol, Caprylyl Glycol | 1.0 | 1.0 |

TABLE 3-continued

| | | w/w % | |
| | | Placebo | |
| | INCI | A | B |
|---|---|---|---|
| | Disodium EDTA | 0.1 | 0.1 |
| | Sodium Chloride | 0.4 | 0.4 |
| B. | Water (Aqua) | 76.2 | 75.2 |
| C. | Potassium Sorbate | 0.15 | 0.15 |
| D. | Cocoamidopropyl Betaine | 5.0 | 5.0 |
| | 3-Hydroxypropyl Caprylate | — | 1.0 |
| | SUM | | 100.0 |

_Hair and body shampoo formulation_

Skin Sensation Evaluation of Hair and Body Shampoo with 1 wt.-% 3-Hydroxypropyl Caprylate Cleaning of the hands by using 1 ml of a standard shampoo and rinsing water Drying of the hands by using a towel Hair and body shampoo (100 µl) was applied by the test manager using an Eppendorf pipette (placebo without active (A) on the left or right index finger, formulation with 1 wt.-% active (B) on the opposite index finger, respectively)

Rubbing of the formulations between thumb, index finger and middle finger for 20 seconds The skin was wetted with rinsing water for 3 seconds Evaluation of the skin sensation in terms of moisturization/re-fattening properties Question to be answered by the panelists:

Which formula (A or B) leads to a more moisturized/re-fattened skin sensation?

Figure 2:
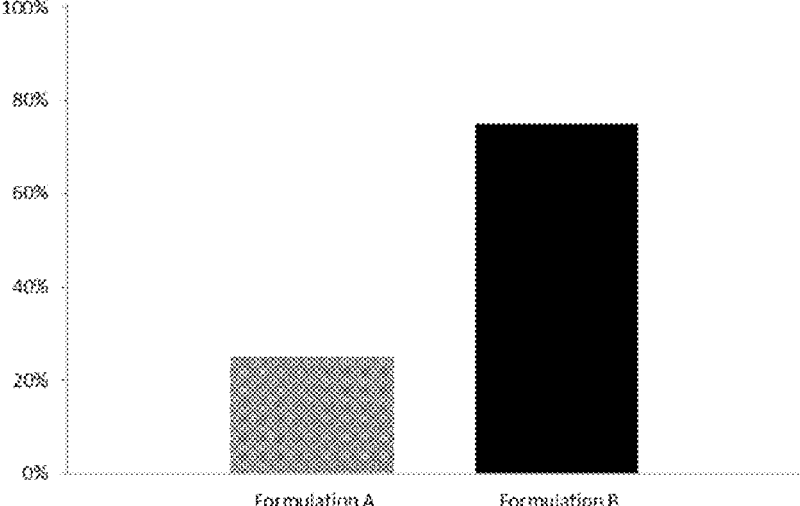
FIG. 2 depicts the percentage distribution of panelist responses in a sensory test evaluating the moisturizing and re-fattening properties of a shampoo formulation containing 1 wt.-% 3-hydroxypropyl caprylate compared with a placebo formulation.

18 subjects out of 24 voted that formulation B containing 1 wt-% 3-hydroxypropyl caprylate is more moisturizing and re-fattening to the skin (cf. Table 4 and FIG. 2).

TABLE 4

Results of evaluation (voting of 24 subjects for sample A or B)

| Number of subjects | Formulation A | Formulation B |
|---|---|---|
| 24 | 6 | 18 |
| % | 25 | 75 |

FIG. 2 depicts the results of the evaluation in % as shown in Table 4 (voting of 24 subjects for A or B).

Foam Behaviour of Hair and Body Shampoo with 1 wt.-% 3-Hydroxypropyl Caprylate Versus Placebo Hands were prewashed with a standard surfactant solution 100 µl sample A or B according to Table 3 (random order) is applied on wet hand (on the left hand for right-hander and vice versa)

Sample is foamed for 20 seconds with index and middle finger

Foam volume is evaluated on scale from 1-5 (1=no foam, 5=most foam; cf. Table 5)

Hands were pre-washed again and the other sample is also evaluated

Question: Which formula shows higher foam volume? (Cf. Table 6 and FIG. 4)

TABLE 5

Results of foam volume evaluation (ranking 0-5; 0 = no foam; 5 = high foam volume)

| Subject No. | Formulation A | Formulation B |
|---|---|---|
| 1 | 3 | 3 |
| 2 | 3 | 4 |
| 3 | 1 | 2 |
| 4 | 4 | 4 |
| 5 | 3 | 3 |
| 6 | 4 | 3 |
| 7 | 3 | 5 |
| 8 | 3 | 5 |
| 9 | 5 | 5 |
| 10 | 1 | 5 |
| 11 | 1 | 2 |
| 13 | 1 | 2 |
| 14 | 5 | 5 |
| 15 | 2 | 3 |
| 16 | 3 | 4 |
| 17 | 4 | 5 |
| 18 | 4 | 4 |
| 19 | 2 | 4 |
| 20 | 2 | 3 |
| 21 | 3 | 4 |
| 22 | 4 | 5 |
| 23 | 1 | 2 |
| 24 | 2 | 3 |
| Arithmetic mean | 2.78 | 3.70 |

Figure 3:
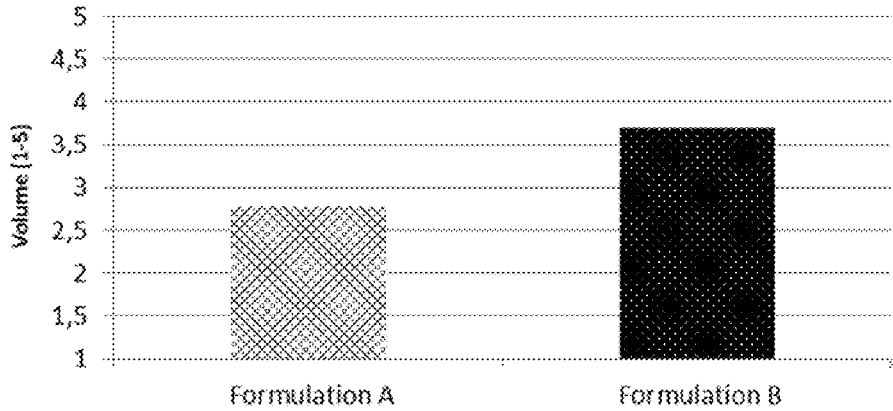
FIG. 3 shows the foam volume ranking results (on a scale of 1-5) for shampoo formulations with and without 1 wt.-% 3-hydroxypropyl caprylate, demonstrating the relative increase in foam volume caused by the active ingredient.

FIG. 3 depicts the results of the foam volume ranking 1-5 (1=low foam volume; 5=high foam volume) as listed in Table 5.

Formulation B containing 1 wt.-% 3-hydroxypropyl caprylate was voted to have higher foam volume (mean value 3.7) than the placebo formulation A without active (mean value 2.8, see Table 5 and FIG. 3 below).

TABLE 6

Results of evaluation (voting of 23 subjects for sample A or B to have higher foam volume)

| Number of subjects | Formulation A | Formulation B |
|---|---|---|
| 23 | 2 | 21 |
| % | 8.7 | 91.3 |

Figure 4:
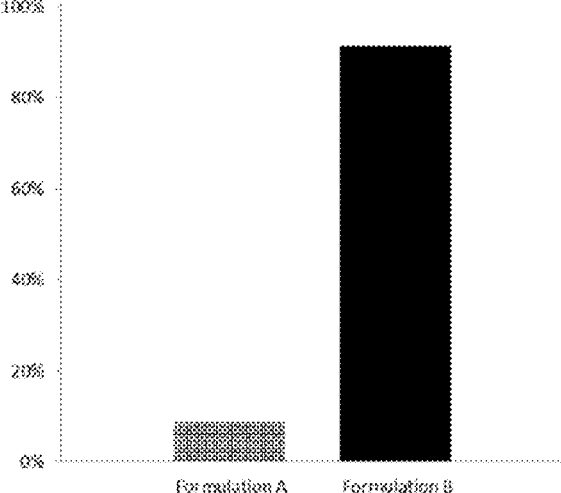
FIG. 4 presents the voting results from panelists indicating which shampoo formulation-placebo or the formulation containing 1 wt.-% 3-hydroxypropyl caprylate-was perceived to generate higher foam volume.

FIG. 4 depicts the results of the evaluation (voting of 24 subjects for sample A or B to have higher foam volume).

It was demonstrated that the addition of 3-hydroxypropyl caprylate leads to higher foam formation in a hair and body wash formulation. 21 subjects out of a panel of 23 subjects voted that formulation B is the formula with the highest foam volume. Only 2 subjects voted that placebo formulation A has a higher foam volume.

3.) Sensory Assessment of 1 wt.-% Glyceryl
Monocaprylate and 1 wt.-% 3-Hydroxypropyl
Caprylate in o/w Emulsion Versus Placebo

TABLE 7

| Emulsion o/w used for sensory assessment | | | |
|---|---|---|---|
| INCI | A1 | A2 | A3 |
| Phase A | | | |
| Potassium Cetyl Phosphate, Hydrogenated Palm Glycerides | 2.0 | 2.0 | 2.0 |
| Pentaerythrityl Distearate | 1.5 | 1.5 | 1.5 |
| Glyceryl Stearate | 2.0 | 2.0 | 2.0 |
| Cetearyl Nonanoate | 3.0 | 3.0 | 3.0 |
| Caprylic/Capric/Triglceride | 7.0 | 7.0 | 7.0 |
| Ethylhexyl Isononanoate | 3.0 | 3.0 | 3.0 |
| Phase B | | | |
| Acrylates/C10-30 Alkyl Acrylate Crosspolymer | 0.2 | 0.2 | 0.2 |
| Xanthan Gum | 0.2 | 0.2 | 0.2 |
| Phase C | | | |
| Water (Aqua) | 74.8 | 74.8 | 74.8 |
| Disodium EDTA | 0.1 | 0.1 | 0.1 |
| Pentyleneglycol | 1.0 | 1.0 | 1.0 |
| 1,2-Hexanediol, Caprylyl Glycol | 0.6 | 0.6 | 0.6 |
| Propylene Glycol | 1.0 | 1.0 | 1.0 |
| Glycerin | 1.0 | 1.0 | 1.0 |
| Phase D | | | |
| Sodium Hydroxide 10% aqueous sol. | 0.6 | 0.6 | 0.6 |
| Phase E | | | |
| Pentyleneglycol | 1.0 | 1.0 | 1.0 |
| Propylene Glycol | 1.0 | 1.0 | 1.0 |
| 3-Hydroxypropyl Caprylate | — | 1.0 | — |
| Glyceryl Monocaprylate | — | — | 1.0 |
| Sum | | 100.0 | |

Heat phase A and C separately up to 80° C. Disperse phase B in A (leading to AB). Add phase C to AB and emulsify using a HomoRex stirrer (5 min, 110 rpm). Add phase D and neutralize. Allow to cool by using a vane stirrer (10 min at 150 rpm, then 20 min at 100 rpm). Pre-dissolve the corresponding active ingredient together with pentylene glycol and propylene glycol and add to the emulsion by using a vane stirrer (10 min, 100 rpm, pH value 5.8).

Test Procedure of Sensory Assessment of 3-Hydroxypropyl Caprylate 1 wt.-% of 3-hydroxypropyl caprylate was incorporated into the o/w emulsion according to table 7 (cf. sample A2).

100 µl of the sample is applied on forearm. Sample is distributed with index and middle finger in rotary movements for 20 seconds. The first two parameters (Whitening and Absorption) are evaluated directly after distribution on a scale from 0-4.

Whitening: 0=not at all; 4=very strongly

Absorption: 0=very slow; 4=extremely speedily

Then the sample is applied on the other forearm and again distributed as described above. After 3 minutes the parameters (velvet/softness, acceptance and soaping) are evaluated on a scale from 0-4. The results of the evaluation are displayed in Table 8.

Soft/velvet/moisturized: 0=not at all; 4=very strong

Acceptance: 0=Dislike; 4=extremely good

Soaping: 0=not at all; 4=very strongly

TABLE 8

Results of sensory evaluation of 3-hydroxypropyl caprylate
(10 untrained panelists)

| | Soaping | | Absorption | |
|---|---|---|---|---|
| | Placebo (A1) | 3-Hydroxypropyl Caprylate 1 wt.-% (A2) | Placebo (A1) | 3-Hydroxypropyl Caprylate 1 wt.-% (A2) |
| | 0 | 0 | 1 | 1 |
| | 3 | 1 | 0 | 3 |
| | 3 | 2 | 1 | 2 |
| | 1 | 1 | 0 | 0 |
| | 3 | 1 | 0 | 1 |
| | 1 | 0 | 1 | 3 |
| | 2 | 1 | 1 | 3 |
| | 3 | 1 | 2 | 2 |
| | 3 | 1 | 1 | 2 |
| | 2 | 1 | 1 | 3 |
| Arithmetic mean | 2.1 | 0.9 | 0.8 | 2.0 |

| | Soft Velvet/Moisturized | | Acceptance | |
|---|---|---|---|---|
| | Placebo (A1) | 3-Hydroxypropyl Caprylate 1 wt-% (A2) | Placebo (A1) | 3-Hydroxypropyl Caprylate 1 wt-% (A2) |
| | 2 | 2 | 2 | 2 |
| | 2 | 1 | 1 | 2 |
| | 2 | 1 | 2 | 2 |
| | 1 | 2 | 0 | 0 |
| | 4 | 1 | 3 | 1 |
| | 0 | 3 | 1 | 3 |
| | 1 | 2 | 1 | 2 |
| | 1 | 3 | 0 | 2 |
| | 2 | 4 | 1 | 2 |
| | 1 | 3 | 0 | 2 |
| Arithmetic mean | 1.6 | 2.2 | 1.1 | 1.8 |

It could be clearly demonstrated that the addition of 1 wt.-% of 3-hydroxypropyl caprylate leads to less soaping of the formulation and to a better absorption versus placebo (formulation A1 without active).

Furthermore, the subjects evaluated that the emulsion with 3-hydroxypropyl caprylate leads to a more soft and a more moisturized skin. The overall acceptance of the active containing emulsion A2 is better than that of placebo A1.

Test Procedure of Sensory Assessment of Glyceryl Mono-caprylate

Samples A1 and A3 (cf. Table 7 above) are applied in a random order on one forearm each. Samples were distributed for 30 seconds with index and middle finger (5 seconds left arm, 5 seconds right arm). After 1 minute, the subjects were asked which sample shows a more caring/rich/moisturizing skin sensation on a scale from 0-4 (0=not at all; 4=very strong; cf. Table 9).

TABLE 9

Results of sensory evaluation of glyceryl monocaprylate
(10 untrained panelists)

| | Caring/Rich/Moisturizing | |
|---|---|---|
| Panelist | Placebo (A1) | 1 wt.-% Glyceryl Monocaprylate (A3) |
| 1 | 2 | 1 |
| 2 | 1 | 4 |
| 3 | 2 | 3 |
| 4 | 1 | 2 |

TABLE 9-continued

Results of sensory evaluation of glyceryl monocaprylate
(10 untrained panelists)

| | Caring/Rich/Moisturizing | |
| Panelist | Placebo (A1) | 1 wt.-% Glyceryl Monocaprylate (A3) |
| --- | --- | --- |
| 5 | 1 | 2 |
| 6 | 1 | 3 |
| 7 | 3 | 2 |
| 8 | 2 | 4 |
| 9 | 2 | 4 |
| 10 | 3 | 4 |
| Aritmetic mean | 1.8 | 2.9 |

Most subjects voted that sample A3 with 1 wt.-% glyceryl monocaprylate has a more caring/rich/moisturized skin sensation.

4.) Sensory Assessment of 1 wt.-% 3-Hydroxypropyl Undecylenate in o/w Emulsion Versus Placebo

TABLE 10

O/w emulsion

| INCI | A (Placebo) | B (1 wt.-% Active) |
| --- | --- | --- |
| Phase A | | |
| Potassium Cetyl Phosphate, Hydrogenated Palm Glycerides | 2.00 | 2.00 |
| Pentaerythrityl Distearate | 1.50 | 1.50 |
| Glyceryl Stearate | 2.00 | 2.00 |
| Cetearyl Nonanoate | 3.00 | 3.00 |
| Caprylic/Capric/Triglceride | 7.00 | 7.00 |
| Ethylhexyl Isononanoate | 3.00 | 3.00 |
| Phase B | | |
| Acrylates/C10-30 Alkyl Acrylate Crosspolymer | 0.20 | 0.20 |
| Xanthan Gum | 0.20 | 0.20 |
| Phase C | | |
| Water (Aqua) | 74.80 | 73.8 |
| Disodium EDTA | 0.10 | 0.10 |
| Pentyleneglycol | 1.00 | 1.00 |
| 1,2-Hexanediol, Caprylyl Glycol | 0.60 | 0.60 |
| Propylene Glycol | 1.00 | 1.00 |
| Glycerin | 1.00 | 1.00 |
| Phase D | | |
| Sodium Hydroxide 10% aqueous sol. | 0.60 | 0.60 |
| Phase E | | |
| Pentylene Glycol | 1.00 | 1.00 |
| Propylene Glycol | 1.00 | 1.00 |
| 3-Hydroxypropyl Undecylenate | — | 1.0 |

Production Method:

Heat phase A and C separately up to 80° C. Disperse phase B in phase A. Add phase C to phase AB and emulsify using a HomoRex stirrer (3 min, 110 rpm). Add phase D and neutralize. Allow to cool by using a vane stirrer (10 min at 150 rpm, then 10 min at 100 rpm). Pre-dissolve 3-hydroxypropyl undecylenate with pentylene glycol and propylene glycol (phase E) and add to the emulsion by using a vane stirrer (10 min, 100 rpm).

Sensory Assessment:

Test design (for two samples; presented in random order) 100 µl of sample was applied on the forearm. Sample was distributed with index and middle finger in rotary movements for 20 seconds. Then the second sample is applied on the other forearm and again distributed. After 3 minutes the skin feel is evaluated.

Question to the panellists:

Which formulation (A or B) leaves the skin more soft and moisturized on a scale from 0-4? (Soft/moisture: 0=not at all; 4=very strong)

TABLE 11

Evaluation results with 10 panelists

| | Soft/Moisturized Skin Feel | |
| | Placebo (A) | 1 wt.-% 3-Hydroxypropyl undecylenate (B) |
| --- | --- | --- |
| | 1 | 3 |
| | 3 | 2 |
| | 2 | 3 |
| | 2 | 3 |
| | 2 | 3 |
| | 2 | 3 |
| | 1 | 3 |
| | 1 | 2 |
| | 2 | 3 |
| | 2 | 3 |
| Arithmetic mean | 1.7 | 2.6* |

*significant versus placebo (P < 0.01)

It could be demonstrated that the addition of 3-hydroxypropyl undecylenate leads to a more soft and moisturized skin feel versus a placebo formulation without active.

5.) Formulation Examples

TABLE 12

Composition of perfume oil 1 (PO1, Amounts in % b.w.)

| Ingredients | Amount |
| --- | --- |
| ALDEHYDE C14 SO-CALLED | 2 |
| ALLYL AMYL GLYCOLATE 10% DPG | 5 |
| ANISIC ALDEHYDE PURE | 5 |
| APPLE OLIFFAC TYPE | 10 |
| Benzylacetate | 50 |
| BERGAMOT IDENTOIL ® COLOURLESS | 15 |
| CANTHOXAL | 5 |
| CETALOX 10% IPM | 3 |
| CITRONELLOL 950 | 40 |
| DAMASCENONE TOTAL 1% DPG | 5 |
| DAMASCONE ALPHA 10% DPG | 5 |
| DAMASCONE DELTA 10% DPG | 2 |
| DIMETHYL BENZYL CARBINYL BUTYRATE | 2 |
| DIPROPYLENE GLYCOL | 178 |
| EBANOL | 2 |
| ETHYL DECADIENOATE TRANS CIS-2,4 10% IPM | 2 |
| FLOROSA | 5 |
| FRAMBINON ® 10% DPG | 7 |
| GALAXOLIDE 50% IN IPM | 100 |
| GALBEX TYPE BASE | 1 |
| GERANYL ACETATE PURE | 2 |
| HEDIONE | 30 |
| HELIOTROPIN | 10 |
| HEXENYL ACETATE CIS-3 10% DPG | 1 |
| HEXENYL SALICYLATE CIS-3 | 5 |
| HEXYL CINNAMIC ALDEHYDE ALPHA | 70 |
| HEXYL SALICYLATE | 50 |
| HYDROXY CITRONELLAL | 10 |
| ISO E SUPER | 15 |

TABLE 12-continued

Composition of perfume oil 1 (PO1, Amounts in % b.w.)

| Ingredients | Amount |
|---|---|
| ISORALDEINE 70 | 20 |
| LEAFOVERT ® | 1 |
| LILIAL | 60 |
| LINALOOL | 60 |
| LINALYL ACETATE | 20 |
| LYRAL | 7 |
| MANZANATE | 2 |
| PHENOXANOL | 7 |
| PHENYLETHYL ALCOHOL | 120 |
| SANDAL MYSORE CORE | 2 |
| SANDRANOL ® | 7 |
| STYRALYL ACETATE | 3 |
| TAGETES RCO 10% TEC | 2 |
| TERPINEOL PURE | 20 |
| TETRAHYDROGERANIOL 10% DPG | 5 |
| TONALIDE | 7 |
| VERTOCITRAL 10% DPG | 5 |
| VERTOFIX | 15 |
| Total | 1000 |

TABLE 13

Composition of perfume oil 2 (PO2, Amounts in % b.w.)

| Ingredients | Amount |
|---|---|
| Acetophenone, 10% in DPG | 10 |
| n-Undecanal | 5 |
| Aldehyde C14, so-called (peach aldehyde) | 15 |
| Allylamyl glycolate, 10% in DPG | 20 |
| Amyl salicylate | 25 |
| Benzyl acetate | 60 |
| Citronellol | 80 |
| d-Limonene | 50 |
| Decenol trans-9 | 15 |
| Dihydromyrcenol | 50 |
| Dimethylbenzylcarbinyl acetate | 30 |
| Diphenyloxide | 5 |
| Eucalyptol | 10 |
| Geraniol | 40 |
| Nerol | 20 |
| Geranium oil | 15 |
| Hexenol cis-3, 10% in DPG | 5 |
| Hexenyl salicylate cis-3 | 20 |
| Indole, 10% in DPG | 10 |
| Alpha-ionone | 15 |
| Beta-ionone | 5 |
| Lilial ® (2-methyl-3-(4-tert-butyl-phenyl)propanal) | 60 |
| Linalool | 40 |
| Methylphenyl acetate | 10 |
| Phenylethyl alcohol | 275 |
| Styrolyl acetate | 20 |
| Terpineol | 30 |
| Tetrahydrolinalool | 50 |
| Cinnamyl alcohol | 10 |
| Total: | 1000 |

TABLE 14

Composition of perfume oil 3 (PO3, Amounts in % b.w.)

| Ingredients | Amount |
|---|---|
| Benzyl acetate | 60 |
| Citronellyl acetate | 60 |
| Cyclamenaldehyde (2-methyl-3-(4-isopropylphenyl) propanal | 20 |
| Dipropylene glycol (DPG) | 60 |
| Ethyllinalool | 40 |

TABLE 14-continued

Composition of perfume oil 3 (PO3, Amounts in % b.w.)

| Ingredients | Amount |
|---|---|
| Florol (2-isobutyl-4-methyltetrahydro-2H-pyran-4-ol) | 30 |
| Globanone ® [(E/Z)-8-cyclohexadecen-1-one] | 180 |
| Hedione ® (methyldihydrojasmonate) | 140 |
| Hexenyl salicylate, cis-3 | 10 |
| Vertocitral (2,4-dimethyl-3-cyclohexenecarboxaldehyde) | 5 |
| Hydratropaldehyde, 10% in DPG | 5 |
| Isodamascone (1-(2,4,4-trimethyl-2-cyclohexen-1-yl)-2-buten-1-one, 10% in DPG | 5 |
| Isomuscone (cyclohexadecanone) | 40 |
| Jacinthaflor (2-methyl-4-phenyl-1,3-dioxolane) | 10 |
| Cis-jasmone, 10% in DPG | 20 |
| Linalool | 50 |
| Linalyl acetate | 30 |
| Methyl benzoate, 10% in DPG | 25 |
| para-Methyl cresol, 10% in DPG | 10 |
| Nerol | 20 |
| Phenylpropylaldehyde | 5 |
| 2-Phenylethyl alcohol | 82 |
| Tetrahydrogeraniol | 13 |
| 2,2-Dimethyl-3-cyclohexyl-1-propanol | 80 |
| Total: | 1000 |

TABLE 15

Composition of perfume oil 4 (PO4, Amounts in % b.w.)

| Ingredients | Amount |
|---|---|
| AMBRETTOLIDE (MACRO) | 10 |
| AMBROXIDE 10% in IPM | 10 |
| BENZYL ACETATE | 20 |
| BENZYL SALICYLATE | 15 |
| BERGAMOT OIL. bergapten-free | 60 |
| CALONE ® 1951 10% in DPG | 15 |
| COUMARIN | 5 |
| CYCLOGALBANATE ® 10% in DPG | 10 |
| ALPHA-DAMASCONE 1% in DPG | 20 |
| DIHYDROMYRCENOL | 10 |
| ETHYL LINALOOL | 75 |
| ETHYL LINALYLACETATE | 50 |
| ETHYL MALTOL 1% in DEP | 10 |
| ETHYLENE BRASSYLATE (MACRO) | 80 |
| FLOROSA | 40 |
| GERANYLACETATE | 10 |
| HEDIONE ® HC/30 | 35 |
| HEDIONE ® | 210 |
| HELIONAL ® | 15 |
| HELVETOLIDE ® (ALICYC) | 30 |
| HEXENYLSALICYLATE CIS-3 | 20 |
| ISO E SUPER ® | 40 |
| LEAFOVERT ® 10% in DEP | 10 |
| LILIAL ® | 80 |
| LYRAL ® | 20 |
| MANDARIN OIL | 10 |
| STYRALYL ACETATE | 5 |
| SYMROSE ® | 15 |
| VANILLIN 10% in DEP | 20 |
| DIPROPYLENE GLYCOL (DPG) | 50 |
| TOTAL | 1000 |

TABLE 16

Composition of perfume oil 5 (PO5, Amounts in % b.w.)

| Ingredients | Amount |
|---|---|
| AMAROCITE ® | 10 |
| AMBROCENIDE ® 10% in DPG | 5 |
| AMBROXIDE | 15 |

TABLE 16-continued

Composition of perfume oil 5 (PO5, Amounts in % b.w.)

| Ingredients | Amount |
|---|---|
| AURELIONE ® (7/8-Cyclohexadecenone) (MACRO) | 70 |
| BERGAMOT OIL. bergapten-free | 90 |
| CALONE ® 1951 10% in DPG | 20 |
| CARAWAY OIL | 10 |
| CITRAL | 20 |
| COUMARIN | 10 |
| ALPHA-DAMASCONE 1% in DPG | 15 |
| DIHYDROMYRCENOL | 70 |
| ESTRAGON OIL | 10 |
| ETHYL LINALOOL | 100 |
| ETHYL LINALYLACETATE | 90 |
| EUGENOL | 10 |
| EVERNYL ® | 5 |
| FRUCTATE ® | 5 |
| GERANIUM OIL | 5 |
| HEDIONE ® HC/30 | 100 |
| HELIONAL ® | 10 |
| INDOLE 10% in DPG | 5 |
| ISO E SUPER ® | 100 |
| KEPHALIS ® | 5 |
| LAVENDER OIL | 40 |
| CITRUS OIL | 80 |
| LILIAL ® | 30 |
| MANDARIN OIL | 20 |
| MUSCENONE (MACRO) | 5 |
| SANDRANOL ® | 10 |
| VANILLIN 10% in DPG | 5 |
| DIPROPYLENE GLYCOL | 30 |
| TOTAL | 1000 |

The perfume oils PO1, PO2, PO3, PO4, or PO5 from the above examples were worked separately in each case into the formulations presented below.

Cosmetic formulations (compositions)—amounts are indicated as % by weight for all formulations.

TABLE 17

Cream o/w

| Ingredients | INCI | Amount |
|---|---|---|
| Dracorin ® CE | Glyceryl Stearate Citrate | 1.0 |
| Lanette ® O | Cetearyl Alcohol | 2.0 |
| Cutina ® GMS-V | Glyceryl Stearate | 1.0 |
| Tegosoft ® MM | Myristyl Myristate | 1.0 |
| Xiameter ® PMX-0246, Cyclosiloxane | Cyclohexasiloxane (and) Cyclopentasiloxane | 0.5 |
| Dragoxat ® 89 | Ethylhexyl Isononanoate | 2.0 |
| PCL-Liquid 100 | Cetearyl Ethylhexanoate | 4.0 |
| Neutral Oil | Caprylic/Capric Triglyceride | 4.0 |
| Carbopol ® Ultrez 21 | Acrylates/C10-30 Alkyl Acrylate Crosspolymer | 0.2 |
| Keltrol ® CG-T | Xanthan Gum | 0.1 |
| Water | Water (Aqua) | ad 100 |
| Glycerol 99, 5 P. | Glycerol | 3.0 |
| 1,2-Propylene Glycol 99 P GC | Propylene Glycol | 2.0 |
| Sodium Benzoate | Sodium Benzoate | 0.1 |
| Sodium Hydroxide 10% solution | Sodium Hydroxide | 0.5 |
| Perfume oil PO1, PO2, PO3, PO4, or PO5 | Perfume | 0.3 |
| Euxyl ® K702 | Dehydroacetic Acid, Benzoic Acid, Phenoxyethanol, Polyaminopropyl Biguanide, Ethylhexylglycerin | 0.3 |
| 3-Hydroxypropyl caprylate | Hydroxypropyl caprylate | 0.3 |
| 3-Hydroxypropyl undecylenate | Hydroxypropyl undecylenate | 0.1 |

TABLE 18

Hand and body cream

| Ingredients | INCI | Amount |
|---|---|---|
| Dracorin ® GOC | Glyceryl Oleate Citrate, Caprylic/Capric Triglyceride | 2.0 |
| PCL-Solid | Stearyl Heptanoate, Stearyl Caprylate | 2.5 |
| Lanette ® O | Cetearyl Alcohol | 1.5 |
| Cutina ® GMS-V | Glyceryl Stearate | 1.0 |
| Dragoxat ® 89 | Ethylhexyl Isononanoate | 3.0 |
| PCL-Liquid 100 | Cetearyl Ethylhexanoate | 7.0 |
| Isodragol ® | Triisononanoin | 4.0 |
| Xiameter ® PMX-0345 Cyclosiloxane | Cyclopentasiloxane (and) Cyclohexasiloxane | 0.5 |
| Water | Water (Aqua) | ad 100 |
| Carbopol ® Ultrez 21 | Acrylates/C10-30 Alkyl Acrylate Crosspolymer | 0.2 |
| Keltrol ® CG-RD | Xanthan Gum | 0.1 |
| Glycerol 85 P. | Glycerol | 3.0 |
| DragoBetaGlucan | Water (Aqua), Butylene Glycol, Glycerol, *Avena Sativa* (Oat) Kernel Extract | 1.5 |
| Potassium Sorbat | Potassium Sorbate | 0.1 |
| Sodium Hydroxide 10% solution | Sodium Hydroxide | 0.5 |
| Perfume oil PO1, PO2, PO3, PO4, or PO5 | Fragrance | 0.2 |
| Euxyl ® K300 | Methyl-, Butyl-, Ethyl-, Propyl, Isobutylparaben, Phenoxyethanol | 0.3 |
| 3-Hydroxypropyl caprylate | Hydroxypropyl caprylate | 0.2 |
| Glyceryl monocaprylate | Glyceryl caprylate | 0.05 |

TABLE 19

Daily face cream SPF 20

| Ingredients | Amount |
|---|---|
| SymOcide PH | 1 |
| Phenoxyethanol, Hydroxyacetophenone, Caprylyl Glycol, Water (Aqua) | |
| Ascorbyl Palmitate | 0.1 |
| Ascorbyl Palmitate | |
| Biotive L-Arginine | 0.2 |
| Arginine | |
| Buriti oil | 1 |
| *Mauritia Flexuosa* Fruit Oil | |
| Cocoa butter | 2 |
| *Theobroma Cacao* (Cocoa) Seed Butter | |
| Dimethicone | 0.5 |
| Dimethicone | |
| Disodium EDTA | 0.1 |
| Disodium EDTA | |
| Dragosantol 100 | 0.1 |
| Bisabolol | |
| Dragoxat 89 | 5 |
| Ethylhexyl Isononanoate | |
| Emulsiphos | 2 |
| Potassium Cetyl Phosphate, Hydrogenated Palm Glycerides | |
| Extrapone Corail | 1 |
| Glycerin, Aqua, Hydrolyzed *Corallina Officinalis* | |
| Glycerin | 3 |
| Glycerin | |
| Isoadipate | 5 |
| Diisopropyl Adipate | |
| Jojoba Wax Flakes | 1 |
| Hydrogenated Jojoba Oil | |
| Keltrol CG-T | 0.1 |
| Xanthan Gum | |
| Lanette O | 5 |
| Cetearyl Alcohol | |
| Lanette 16 | 1 |
| Cetyl Alcohol | |

TABLE 19-continued

| Daily face cream SPF 20 | |
|---|---|
| Ingredients | Amount |
| Lanette 22 | 1 |
| Behenyl Alcohol | |
| Neo Heliopan 357 | 3 |
| Butyl Methoxydibenzoylmethane | |
| Neo Heliopan HMS | 10 |
| Homosalate | |
| Neo Heliopan Hydro used as a 25% aq. Solution | 8 |
| neutralized by arginine | |
| Phenylbenzimidazole Sulfonic Acid | |
| Neo Heliopan OS | 5 |
| Ethylhexyl Salicylate | |
| Orgasol Caresse | 1 |
| Polyamide-5 | |
| Perfume oil PO1, PO2, PO3, PO4, or PO5 | 0.1 |
| Shea butter | 3 |
| *Butyrospermum Parkii* (Shea) Butter | |
| Simugel EG | 1 |
| Sodium Acrylate/Sodium Acryloyldimethyl Taurate | |
| Copolymer, Isohexadecane, Polysorbate 80 | |
| SymFinity 1298 | 0.1 |
| *Echinacea Purpurea* Extract | |
| SymMatrix | 0.1 |
| Maltodextrin, *Rubus Fructicosus* (Blackberry) Leaf | |
| Extract | |
| SymSitive 1609 | 1 |
| Pentylene Glycol, 4-t-Butylcyclohexanol | |
| Tegosoft TN | 4 |
| C12-15 Alkyl Benzoate | |
| 3-Hydroxypropyl caprylate | 0.3 |
| Glyceryl monoundecylenate | 0.1 |
| Water | ad 100 |
| Aqua | |

TABLE 20

| w/o night cream | | |
|---|---|---|
| Ingredients | INCI | Amount |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Aloe Vera Gel Concentrate 10/1 * | Water (Aqua), *Aloe Barbadensis* Leaf Juice | 3.0 |
| Alugel 34 TH | Aluminium Stearate | 1.0 |
| Dragosan W/O P* | Sorbitan Isostearate, Hydrogenated Castor Oil, Ceresin, Beeswax (*Cera Alba*) | 6.0 |
| Dragosantol ® 100* | Bisabolol | 0.2 |
| Extrapone ® Witch Hazel Distillate colourless | Propylene Glycol, *Hamamelis Virginiana* (Witch Hazel) Water, Water (Aqua), *Hamamelis Virginiana* (Witch Hazel) Extract | 1.0 |
| Perfume oil PO1, PO2, PO3, PO4, or PO5 | Fragrance | 0.4 |
| Glycerol 85% | Glycerin | 2.0 |
| Karion F | Sorbitol | 2.0 |
| Magnesium Chloride | Magnesium Chloride | 0.7 |
| PCL Liquid 100 | Cetearyl Ethylhexoate | 12.0 |
| Retinyl Palmitate in Oil | Retinyl Palmitate | 0.2 |
| Sun Flower Oil | *Helianthus Annuus* (Sunflower) Seed Oil | 5.0 |
| Sweet Almond Oil | *Prunus dulcis* | 5.0 |
| SymMatrix ® | Maltodextrin, *Rubus Fruticosus* (Blackberry) Leaf Extract | 1.0 |
| SymOcide PS | Phenoxyethanol, Decylene glycol, 1,2-Hexanediol | 1.0 |
| SymVital ® AgeRepair | *Zingiber Officinale* (Ginger) Root Extract | 0.1 |
| Tocopherol Acetate | Tocopheryl Acetate | 3.0 |
| Water (demineralized) | Water (Aqua) | ad 100 |

TABLE 21

| Body lotion | |
|---|---|
| Ingredients | Amount |
| Cetearyl Alcohol | 2.0 |
| Ethylhexyl Isononanoate | 5.0 |
| Cetearyl Ethylhexanoate, Isopropyl Myristate | 3.0 |
| Glyceryl Oleate Citrate, Caprylic/Capric Triglyceride | 4.0 |
| Water (Aqua) | ad 100 |
| Carbomer | 0.3 |
| Sodium Benzoate | 0.1 |
| Propylene Glycol | 5.0 |
| Sodium Hydroxide 30% solution | 0.3 |
| Perfume oil PO1, PO2, PO3, PO4, or PO5 | 0.3 |
| Triethylene Glycol, Imidazolidinyl Urea, Methylparaben, Propyl-paraben, Dehydroacetic Acid | 0.3 |
| 3-Hydroxypropyl caprylate | 0.2 |
| 3-Hydroxypropyl undecylenate | 0.2 |

TABLE 22

| Antibacterial body lotion, sprayable | | |
|---|---|---|
| Ingredients | INCI | Amount |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| 2,4-Hexadienoic acid, potassium salt | Sorbic acid, potassium salt | 0.2 |
| Dow Corning 345 Fluid | Cyclomethicone | 0.5 |
| Dracorin ® GOC | Glyceryl Oleate Citrate, Caprylic/Capric Triglyceride | 2.0 |
| Drago-Calm | Water, Glycerin, *Avena Sativa* (Oat) Kernel Extract | 1.0 |
| Dragosantol ® 100* | Bisabolol | 0.1 |
| Perfume oil PO1, PO2, PO3, PO4, or PO5 | Fragrance | 0.3 |
| Hydrolite ®-5 | Pentylene Glycol | 5.0 |
| Neutral Oil | Caprylic/Capric Triglyceride | 4.0 |
| Paraffin Oil | Mineral Oil | 4.0 |
| PCL Liquid 100 | Cetearyl Ethylhexoate | 7.0 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymDeo ® MPP | Dimethyl Phenylbutanol | 0.5 |
| SymRelief ® 100 | Bisabolol, *Zingiber Officinale* (Ginger) Root Extract | 0.1 |
| Water (demineralized) | Water (Aqua) | ad 100 |

TABLE 23

| Aseptic wound cream | |
|---|---|
| Ingredients | Amount |
| Sorbitan Isostearate, Hydrogenated Castor Oil, Ceresin, Beeswax (Cera Alba) | 6.0 |
| Petrolatum | 21.0 |
| Cera Alba | 5.0 |
| Cetearyl Alcohol | 7.0 |
| *Prunus Dulcis* | 7.0 |
| Lanolin | 5.0 |
| Paraffinum Liquidum | 12.0 |
| Perfume oil PO1, PO2, PO3, PO4, or PO5 | 0.3 |
| Water (Aqua) | ad 100 |
| Panthenol | 7.0 |
| Magnesium Sulfate | 0.7 |
| Pentylene Glycol | 1.0 |
| Tocopheryl Acetate | 1.0 |
| Octenidine dihydrochloride | 0.1 |
| Phenoxyethanol | 0.5 |

TABLE 23-continued

Aseptic wound cream

| Ingredients | Amount |
|---|---|
| 3-Hydroxypropyl caprylate | 0.4 |
| Glyceryl monocaprylate | 0.2 |

TABLE 24

Anti acne balm

| Ingredients | INCI | Amount |
|---|---|---|
| 3-Hydroxypropyl caprylate | Hydroxypropyl caprylate | 0.3 |
| 3-Hydroxypropyl undecylenate | Hydroxypropyl undecylenate | 0.2 |
| Abil 350 | Dimethicone | 1.0 |
| Allantoin | Allantoin | 0.1 |
| Aloe Vera Gel Concentrate 10/1 * | Water (Aqua), Aloe *Barbadensis* Leaf Juice | 3.0 |
| Azelaic Acid | Azelaic Acid | 5.0 |
| Cetiol OE | Dicaprylyl Ether | 4.0 |
| Cetiol SB 45 | *Butyrospermum Parkii* (Shea Butter) | 1.0 |
| D-Panthenol | Panthenol | 1.0 |
| Emulsiphos ® | Potassium Cetyl Phosphate, Hydrogenated Palm Glycerides | 2.0 |
| Perfume oil PO1, PO2, PO3, PO4, or PO5 | Fragrance | 0.2 |
| Frescolat ®ML cryst. | Menthyl Lactate | 0.8 |
| Glycerol 85% | Glycerin | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Lara Care A-200 | Galactoarabinan | 0.3 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymOcide PH | Hydroxyacetophenone, Phenoxyethanol, Caprylyl glycol, Aqua | 1.0 |
| Tegosoft TN | C12-15 Alkyl Benzoate | 5.0 |
| Tocopherol Acetate | Tocopheryl Acetate | 0.5 |
| Water (demineralized) | Water (Aqua) | ad 100 |

TABLE 25

Barrier repair cream

| Ingredients | INCI | Amount |
|---|---|---|
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.1 |
| Glyceryl monoundecylenate | Glyceryl undecylenate | 0.1 |
| Abil 350 | Dimethicone | 0.5 |
| Allantoin | Allantoin | 0.25 |
| Ceramide BIO* | Cetylhydroxproline Palmitamide | 0.5 |
| Dracorin ® CE | Glyceryl Stearate Citrate | 1.5 |
| Dragoxat ® 89 | Ethylhexyl Ethylisononan-oate | 2.0 |
| Emulsiphos ® | Potassium Cetyl Phosphate, Hydrogenated Palm Glycerides | 2.0 |
| Extrapone ® Rosemary GW | Glycerin, Water (Aqua), *Rosmarinus officinalis* (Rosemary) Leaf Extract | 0.5 |

TABLE 25-continued

Barrier repair cream

| Ingredients | INCI | Amount |
|---|---|---|
| Perfume oil PO1, PO2, PO3, PO4, or PO5 | Fragrance | 0.1 |
| Glycerol 85% | Glycerin | 3.0 |
| Glyceryl Stearate | Glyceryl Stearate | 2.0 |
| Hydroviton ® 24 | Water, Glycerin, Sodium Lactate, TEA Lactate, Serine, Lactic Acid, Urea, Sorbitol, Sodium Chloride, Lauryl Diethylenedi-aminoglycine, Lauryl Aminopropyl-glycine, Allantoin | 1.0 |
| Isodragol ® | Triisononanoin | 3.0 |
| Lanette O | Cetearyl Alcohol | 2.0 |
| NaOH 10% sol. | Sodium Hydroxide | 0.3 |
| Neutral Oil | Caprylic/Capric Triglyceride | 10.0 |
| SymCalmin ® | Pentylene Glycol, Butylene Glycol, Hydroxyphenyl Propamidobenzoic Acid | 1.0 |
| SymRepair ® 100 | Hexyldecanol, Bisabolol, Cetylhydroxyproline Palmitamide, Stearic Acid, *Brassica Campestris* (Rapeseed) Sterols | 2.0 |
| SymTriol | Caprylyl glycol, 1,2-Hexanediol, Methylbenzyl alcohol | 1.0 |
| Tegosoft PC 31 | Polyglyceryl 3-Caprate | 0.3 |
| Tocopherol Acetate | Tocopheryl Acetate | 0.3 |
| Water (demineralized) | Water (Aqua) | ad 100 |

TABLE 26

Skin soothing lotion

| Ingredients | INCI | Amount |
|---|---|---|
| 3-Hydroxypropyl caprylate | Hydroxypropyl caprylate | 0.3 |
| Glyceryl monocaprylate | Glyceryl caprylate | 0.05 |
| 3-Hydroxypropyl undecylenate | Hydroxypropyl undecylenate | 0.2 |
| Glyceryl monoundecylenate | Glyceryl undecylenate | 0.05 |
| Abil 350 | Dimethicone | 2.0 |
| Allantoin | Allantoin | 0.2 |
| Carbopol Ultrez-10 | Carbomer | 0.1 |
| Ceramide BIO* | Cetylhydroxyproline Palmitamide | 0.1 |
| Citric Acid 10% sol. | Citric Acid | 0.4 |
| Emulsiphos ® | Potassium Cetyl Phosphate, Hydrogenated Palm Glycerides | 2.0 |
| Extrapone ® Green Tea GW | Glycerin, Water (Aqua), *Camellia Sinensis* Leaf Extract | 0.2 |
| Extrapone ® Rosemary GW | Glycerin, Water (Aqua), *Rosmarinus officinalis* (Rosemary) Leaf Extract | 0.3 |
| Perfume oil PO1, PO2, PO3, PO4, or PO5 | Fragrance | 0.3 |
| Glycerol 85% | Glycerin | 2.0 |
| Glyceryl Stearate | Glyceryl Stearate | 2.0 |
| Isodragol ® | Triisononanoin | 2.0 |
| Keltrol RD | Xanthan Gum | 0.1 |
| Lanette O | Cetearyl Alcohol | 3.0 |
| Neo PCL wssl. N | Trideceth-9, PEG-5 Ethylhexanoate, Water | 1.0 |
| PCL Liquid 100 | Cetearyl Ethylhexanoate | 5.0 |
| PCL Solid | Stearyl Heptanoate, Stearyl Caprylate | 2.0 |
| Propylene Glycol | Propylene Glycol | 5.0 |
| Sodium Hydroxide (10% sol.) | Sodium Hydroxide | 0.3 |
| SymCalmin ® | Pentylene Glycol, Butylene Glycol, Hydroxyphenyl Propamidobenzoic Acid | 2.0 |
| SymMatrix ® | Maltodextrin, *Rubus Fruticosus* (Blackberry) Leaf Extract | 0.1 |
| SymSave H | Hydroxyacetophenone | 0.4 |

TABLE 26-continued

| Skin soothing lotion | | |
| --- | --- | --- |
| Ingredients | INCI | Amount |
| 2-Phenoxyethyl Alcohol | Phenoxyethanol | 0.4 |
| SymSitive ®1609 | Pentylene Glycol, 4-t-Butylcyclohexanol | 1.5 |
| Water (demineralized) | Water (Aqua) | ad 100 |

TABLE 27

| Baby Nappy Rash Cream w/o | |
| --- | --- |
| Ingredients | Amount |
| SymOcide PH<br>Phenoxyethanol, Hydroxyacetophenone,<br>Caprylyl Glycol, Water<br>(Aqua) | 1 |
| Cupuaçu butter<br>Theobroma Grandiflorum Seed Butter | 1 |
| Cutina HR Powder<br>Hydrogenated Castor Oil | 1.5 |
| Dehymuls PGPH<br>Polyglyceryl-2 Dipolyhydroxystearate | 5 |
| Glycerin<br>Glycerin | 5 |
| Jojoba oil<br>Simmondsia Chinensis (Jojoba) Seed Oil | 5 |
| Magnesium Sulfate Hepta Hydrate<br>Magnesium Sulfate | 0.5 |
| Monomuls 90-O18<br>Glyceryl Oleate | 1 |
| Neutral oil<br>Caprylic/capric triglyceride | 8 |
| PCL Liquid 100<br>Cetearyl Ethylhexanoate | 5 |
| SymCalmin<br>Butylene Glycol, Pentylene<br>Glycol, Hydroxyphenyl<br>Propamidobenzoic Acid | 1 |
| Tamanu oil<br>Calophyllum Inophyllum Seed Oil | 0.2 |
| Tetrasodium EDTA<br>Tetrasodium EDTA | 0.1 |
| Titan dioxide<br>Titan dioxide | 4 |
| Water<br>Aqua | ad 100 |
| Wheat germ oil<br>Triticum Vulgare (Wheat) Germ Oil | 2 |
| Zinc oxide<br>Zinc oxide | 10 |
| 3-Hydroxypropyl caprylate | 0.3 |
| 3-Hydroxypropyl undecylenate | 0.15 |

TABLE 28

| Skin lightening day cream o/w | | |
| --- | --- | --- |
| Ingredients | INCI | Amount |
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.5 |
| Dracorin ® CE | Glyceryl Stearate Citrate | 2.5 |
| Dracorin ® GOC | Glyceryl Oleate Citrate, Caprylic/Capric Triglyceride | 0.5 |

TABLE 28-continued

| Skin lightening day cream o/w | | |
| --- | --- | --- |
| Ingredients | INCI | Amount |
| Drago-Beta-Glucan | Water (Aqua), Butylene Glycol, Glycerin, Avena Sativa (Oat), Kernel Extract | 0.3 |
| Dragosantol ® 100* | Bisabolol | 0.2 |
| Perfume oil PO1, PO2, PO3, PO4, or PO5 | Fragrance | 0.1 |
| Frescolat ® MGA | Menthone Glycerol Acetal | 0.5 |
| Glycerol 85% | Glycerin | 3.0 |
| Isopropyl Palmitate | Isopropyl Palmitate | 4.0 |
| Keltrol RD | Xanthan Gum | 0.2 |
| Lanette 16 | Cetyl Alcohol | 1.0 |
| Neo Heliopan ® AV | Ethylhexyl Methoxy-cinnamate | 5.0 |
| Neutral Oil | Caprylic/Capric Triglyceride | 6.0 |
| PCL Liquid 100 | Cetearyl Ethylhexoate | 3.0 |
| Sodium Benzoate | Sodium Benzoate | 0.1 |
| Symdiol ®68T | 1,2-Hexanediol, Caprylylglycol, Tropolone | 0.5 |
| SymVital ® AgeRepair | Zingiber Officinale (Ginger) Root Extract | 0.1 |
| SymWhite ®377 | Phenylethyl Resorcinol | 0.5 |
| Water (demineralized) | Water (Aqua) | ad 100 |

TABLE 29

| Shampoo | |
| --- | --- |
| Ingredients | Amount |
| 4-Hydroxyacetophenone (SymSave H)<br>Hydroxyacetophenone | 0.3 |
| Antil 127<br>PEG-120 Methyl Glucose Dioleate | 0.5 |
| Brazilian nut oil<br>Bertholletia Excelsa Seed Oil | 0.5 |
| Cocamidopropyl Betaine 38%<br>Cocamidopropyl Betaine | 5 |
| Octopirox<br>Piroctone olamine | 0.3 |
| Dragoderm<br>Glycerin, Triticum Vulgare Gluten, Aqua | 0.5 |
| Fragrance<br>Perfum | 0.5 |
| Glycerin<br>Glycerin | 0.5 |
| Jojoba oil<br>Simmondsia Chinensis (Jojoba) Seed Oil | 0.5 |
| Marlinat 242/90M<br>MIPA Laureth Sulfate, Propylene Glycol | 15 |
| Marlowet CG<br>PEG-18 Castor Oil Dioleate | 2 |
| Plantacare 1200 UP<br>Lauryl Glucoside | 0.5 |
| Polyquaternium-10<br>Polyquaternium-10 | 0.3 |
| Sodium Chloride<br>Sodium Chloride | 1.5 |
| SymCalmin<br>Butylene Glycol, Pentylene Glycol, Hydroxyphenyl<br>Propamidobenzoic Acid | 1 |
| SymOcide PS<br>Phenoxyethanol, Decylene Glycol,1,2-Hexanediol | 0.8 |
| 3-Hydroxypropyl caprylate | 0.4 |
| 3-Hydroxypropyl undecylenate | 0.2 |
| Water<br>Aqua | ad 100 |

TABLE 30

Anti dandruff shampoo

| Ingredients | INCI | Amount |
|---|---|---|
| 3-Hydroxypropyl caprylate | Hydroxypropyl caprylate | 0.3 |
| Glyceryl monocaprylate | Glyceryl caprylate | 0.2 |
| 3-Hydroxypropyl undecylenate | Hydroxypropyl undecylenate | 0.15 |
| Aloe Vera Gel Concentrate 10/1 * | Water (Aqua), *Aloe Barbadensis* Leaf Juice | 0.5 |
| Avocado oil | *Persea Gratissima* (Avocado) Oil | 0.5 |
| Citric Acid 10% sol. | Citric Acid | 0.3 |
| Comperlan 100 | Cocamide MEA | 0.5 |
| Crinipan AD | Climbazole | 0.2 |
| Dragoderm ® | Glycerin, *Triticum Vulgare* (Wheat) Gluten, Water (Aqua) | 2.0 |
| Perfume oil PO1, PO2, PO3, PO4, or PO5 | Fragrance | 0.5 |
| Genapol LRO liquid | Sodium Laureth Sulfate | 37.0 |
| Merquat 550 | Polyquaternium-7 | 0.5 |
| Sodium Chloride | Sodium Chloride | 1.0 |
| SymSave ® H | Hydroxyacetophenone | 0.8 |
| Tego Betain L7 | Cocamidopropyl Betaine | 6.0 |
| Water (demineralized) | Water (Aqua) | ad 100 |

TABLE 31

2-in-1 Shampoo

| Ingredients | INCI Name | Amount |
|---|---|---|
| Deionized water | Water | ad 100 |
| Shea butter | *Butyrospermum Parkii* (Shea) Butter | 0.1 |
| Plantacare PS 10 | Sodium Laureth Sulfate, Lauryl Glucoside | 20.0 |
| Euperlan PK 771 | Glycol Distearate, Sodium Lauryl Sulfate, Cocamide MEA, Laureth-10 | 6.0 |
| Sodium chloride | Sodium Chloride | 1.4 |
| Citric acid monohydrate crystalline | Citric acid | 0.1 |
| Perfume oil PO1, PO2, PO3, PO4, or PO5 | Fragrance | 0.5 |
| Phenoxyethanol, Methylparaben, Ethylparaben | Phenoxyethanol, Methylparaben, Ethylparaben | 0.5 |
| Zinc Omadine | Zinc pyrithione | 0.10 |
| 3-Hydroxypropyl caprylate | Hydroxypropyl caprylate | 0.3 |
| 3-Hydroxypropyl undecylenate | Hydroxypropyl undecylenate | 0.15 |

TABLE 32

Body wash

| Ingredients | INCI | Amount |
|---|---|---|
| Lumerol K 28 | Disodium Laureth Sulfosuccinate, Cocamidopropyl Betaine, Magnesium Lauryl Sulfate | 33.0 |
| Amphotensid B 4 | Cocamidopropyl Betaine | 10.0 |
| Perlglanzmittel GM 4055 | MIPA-Pareth-25 Sulfate, Glycol Stearate | 4.0 |
| Sodium Chloride | Sodium Chloride | 2.0 |
| Avocado oil | *Persea Gratissima* (Avocado) Oil | 3.0 |
| SymSave H | Hydroxyacetophenone | 0.8 |
| Water | Water | ad 100 |
| Perfume oil PO1, PO2, PO3, PO4, or PO5 | Fragrance | 0.5 |
| 3-Hydroxypropyl caprylate | Hydroxypropyl caprylate | 0.15 |
| Glyceryl monocaprylate | Glyceryl caprylate | 0.15 |

TABLE 32-continued

Body wash

| Ingredients | INCI | Amount |
|---|---|---|
| 3-Hydroxypropyl undecylenate | Hydroxypropyl undecylenate | 0.1 |
| Glyceryl monoundecylenate | Glyceryl undecylenate | 0.1 |

TABLE 33

Shower gel

| Ingredients | INCI | Amount |
|---|---|---|
| Deionized water | Water | ad 100 |
| Shea butter | *Butyrospermum Parkii* (Shea) Butter | 1.0 |
| Plantacare PS 10 | Sodium Laureth Sulfate, Lauryl Glucoside | 20.0 |
| Dehydroacetic acid | Dehydroacetic acid | 0.2 |
| SymSave H | Hydroxyacetophenone | 0.3 |
| Sodium chloride | Sodium Chloride | 1.4 |
| Citric acid monohydrate crystalline | Citric Acid | 1.3 |
| Perfume oil PO1, PO2, PO3, PO4, or PO5 | Fragrance | 0.6 |
| 3-Hydroxypropyl caprylate | Hydroxypropyl caprylate | 0.1 |
| Glyceryl monocaprylate | Glyceryl caprylate | 0.3 |
| 3-Hydroxypropyl undecylenate | Hydroxypropyl undecylenate | 0.2 |

TABLE 34

Intimate wash

| Ingredients | INCI | Amount |
|---|---|---|
| Tegobetaine HS | Cocamidopropyl Betaine, Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic Acid, 80% | Lactic Acid | 0.1 |
| euxyl ® K700 | Potassium Sorbate, Benzyl Alcohol, Phenoxyethanol | 0.3 |
| Water | Water | ad 100 |
| Perfume oil PO1, PO2, PO3, PO4, or PO5 | Fragrance | 0.2 |
| 3-Hydroxypropyl caprylate | Hydroxypropyl caprylate | 0.3 |
| Glyceryl monocaprylate | Glyceryl caprylate | 0.1 |
| 3-Hydroxypropyl undecylenate | Hydroxypropyl undecylenate | 0.1 |
| Glyceryl monoundecylenate | Glyceryl undecylenate | 0.05 |

TABLE 35

Liquid soap, transparent

| Ingredients | INCI | Amount |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate, 28% | Sodium Laureth Sulfate | 35.0 |
| Tego-Betaine L7 | Cocamidopropyl Betaine | 5.0 |
| Soap, 25% | Coconut acid, Potassium salt, Potassium Oleate | 20.0 |
| Perfume oil PO1, PO2, PO3, PO4, or PO5 | Fragrance | 0.4 |
| Preservative | DMDM Hydantoin | 0.2 |

TABLE 35-continued

Liquid soap, transparent

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| Water | Water | ad 100 |

TABLE 36

Syndet soap, liquid

| Ingredients | INCI | Amount |
|---|---|---|
| Elfan OS 46 | Sodium Olefin C14-C16 Sulfonate | 35.5 |
| Armoteric LB | Lauryl Betaine | 8.0 |
| Euperlan PK 3000 OK | Glycol Distearate, Glycerin, Laureth-4, Cocamidopropyl Betaine | 10.0 |
| Elfacos GT 282 L | Talloweth-60 Myristyl Glycol | 3.0 |
| PCL-Liquid 100 | Cetearyl Ethylhexanoate | 4.0 |
| Perfume oil PO1, PO2, PO3, PO4, or PO5 | Fragrance | 0.4 |
| SymSave H | 4-Hydroxyacetophenone | 0.6 |
| 3-Hydroxypropyl caprylate | Hydroxypropyl caprylate | 0.15 |
| 3-Hydroxypropyl undecylenate | Hydroxypropyl undecylenate | 0.25 |
| Water | Water | ad 100 |

TABLE 37

Anti-acne wash

| Ingredients | Amount |
|---|---|
| Water (Aqua) | ad 100 |
| Polyquaternium-7 | 0.5 |
| Cocamidopropyl Betaine | 9.0 |
| Coco Glucoside | 2.0 |
| Polysorbate 80, Glycerol, *Gossypium Herbaceum*, (Cotton) Seed Oil, Water (Aqua) | 1.0 |
| Trideceth-9, PEG-5 Ethylhexanoate, Water (Aqua) | 1.0 |
| Glycereth-90 Isostearate, Laureth-2 | 0.5 |
| Sodium Laureth Sulfate | 37.0 |
| Glycerol, *Triticum Vulgare* (Wheat) Gluten, Water (Aqua) | 1.0 |
| Sodium Chloride | 0.3 |
| Perfume oil PO1, PO2, PO3, PO4, or PO5 | 1.0 |
| SymOcide BHO (Hydroxyacetophenone, Benzyl alcohol, Caprylyl glycol, Water) | 1.0 |
| 3-Hydroxypropyl caprylate | 0.25 |
| 3-Hydroxypropyl undecylenate | 0.15 |

TABLE 38

Mineral wash and cleaning gel

| Ingredients | INCI | Amount |
|---|---|---|
| Water | Water (Aqua) | ad 100 |
| Pionier ® NP 37 G | Sodium Carbomer | 1.5 |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 5.0 |
| Hydroviton ® 24 | Water (Aqua), Pentylene Glycol, Glycerol, Sodium Lactate, Lactic Acid, Serine, Urea, Sorbitol, Sodium Chloride, Allantoin | 1.0 |
| Extrapone ® Silk GW | Water (Aqua), Glycerol, Hydrolyzed Silk | 1.0 |
| Hydrolite ® 5 | Pentylene Glycol | 4.0 |
| Actipearls Red Star # | Water (Aqua), Propylene Glycol, Algin, | 1.0 |

TABLE 38-continued

Mineral wash and cleaning gel

| Ingredients | INCI | Amount |
|---|---|---|
| DH10402/6 | Gellan Gum, Xanthan Gum, CalciumChloride, CI 12490 (Pigment Red 5), Mica (CI 77019), Titanium Dioxide (CI 77891) | |
| Perfume oil PO1, PO2, PO3, PO4, or PO5 | Fragrance | 0.5 |
| SymGuard CD | Phenylpropanol, o-cymen-5-ol, Decylene glycol | 0.3 |
| 3-Hydroxypropyl caprylate | Hydroxypropyl caprylate | 0.2 |
| 3-Hydroxypropyl undecylenate | Hydroxypropyl undecylenate | 0.1 |

TABLE 39

After Shave Tonic

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, SodiumOleate, Sodium Sulfate | 3.0 |
| SymSitive ® 1609 | Pentylene Glycol, 4-t-Butylcyclohexanol | 1.0 |
| Frescolat ® ML | Menthyl Lactate | 0.3 |
| Glycerol 99, 5 P. | Glycerol | 5.0 |
| Water | Water (Aqua) | ad 100 |
| Extrapone ® Glacier Water GW | Glycerol, Water (Aqua) | 1.0 |
| SymCalmin ® | Butylene Glycol, Pentylene Glycol, Hydroxyphenyl Propamidobenzoic Acid | 0.5 |
| Dragosine ® | Carnosine | 0.1 |
| Hydrolite ® 5 | Pentylene Glycol | 5.0 |
| Ethanol 96% | Alcohol Denat. | 5.0 |
| Colour Pigment | Colour Pigment | 0.05 |
| Perfume oil PO1, PO2, PO3, PO4, or PO5 | Fragrance | 0.15 |
| 3-Hydroxypropyl caprylate | Hydroxypropyl caprylate | 0.1 |
| 3-Hydroxypropyl undecylenate | Hydroxypropyl undecylenate | 0.05 |

TABLE 40

Hair conditioner with Crinipan, rinse-off

| Ingredients | INCI | Amount |
|---|---|---|
| Lanette ® O | Cetearyl Alcohol | 4.0 |
| Dragoxat 89 | Ethylhexyl Isononanoate | 2.0 |
| Genamin ® KDM-P | Behentrimonium Chloride | 1.0 |
| SF 1550 | Phenyl Trimethicone | 0.1 |
| Neo Heliopan ® BB | Benzophenone-3 | 0.1 |
| Crinipan ® AD | Climbazole | 0.4 |
| Glycerol 99, 5 P. | Glycerol | 6.0 |
| Water | Water (Aqua) | ad 100 |
| Actipone ® Alpha Pulp | Water (Aqua), Butylene Glycol, Malic Acid, *Actinidia Chinensis* (Kiwi) Fruit Juice, Citrus *Aurantium Dulcis* (Orange) Juice, *Citrus Paradisi* (Grapefruit) Juice, *Pyrus Malus* (Apple) Juice, Trideceth-9, *Prunus Amygdalus Dulcis* (Sweet Almond) Seed Extract | 0.5 |

TABLE 40-continued

Hair conditioner with Crinipan, rinse-off

| Ingredients | INCI | Amount |
|---|---|---|
| Extrapone ® Bamboo P | Propylene Glycol, Water (Aqua), Butylene Glycol, *Bambusa Vulgaris* Shoot Extract | 0.5 |
| Sodium Hydroxide 10% solution | Sodium Hydroxide | 0.4 |
| Colour I | Colour | 0.6 |
| Colour II | Colour | 0.3 |
| Perfume oil PO1, PO2, PO3, PO4, or PO5 | Fragrance | 0.4 |
| Preservative | Methylparaben | 0.3 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.15 |

TABLE 41

Scalp soothing hair conditioner with UV-B/UV-A protection, rinse off

| Ingredients | INCI | Amount |
|---|---|---|
| 3-Hydroxypropyl caprylate | Hydroxypropyl caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |
| Abil 350 | Dimethicone | 0.1 |
| Dehyquart A CA | Cetrimonium Chloride | 0.5 |
| Dehyquart SP | Quaternium-52 | 4.0 |
| Dracorin ® CE | Glyceryl Stearate Citrate | 1.0 |
| EDETA BD | Disodium EDTA | 0.1 |
| Extrapone ® Green Tea GW | Glycerin, Water (Aqua), *Camellia Sinensis* Leaf Extract | 0.7 |
| Perfume oil PO1, PO2, PO3, PO4, or PO5 | Fragrance | 0.5 |
| Lara Care A-200 | Galactoarabinan | 0.5 |
| Neutral Oil | Caprylic/Capric Triglyceride | 1.0 |
| PCL Liquid 100 | Cetearyl Ethylhexoate | 0.3 |
| PCL Solid | Stearyl Heptanoate, Stearyl Caprylate | 3.0 |
| SymOcide ® PS | Phenoxyethanol, Decylene Glycol, 1,2-Hexanediol | 1.0 |
| Water (demineralized) | Water (Aqua) | ad 100 |

TABLE 42

Hair conditioner with UV protection

| Ingredients | INCI | Amount |
|---|---|---|
| Renex PEG 6000 | PEG-150 | 2.5 |
| Hair Conditioner Base | Cetyl alcohol, behentrimonium chloride, *Triticum Vulgare* (Wheat) bran extract, linoleic acid | 3.0 |
| PCL-Solid | Stearyl heptanoate, stearyl caprylate | 0.5 |
| Dow Corning 5200 | Laurylmethicone copolyol | 0.5 |
| Natrosol 250 HR | Hydroxyethylcellulose | 0.5 |
| Benzophenone-4 | Benzophenone-4 | 1.0 |
| Neo Heliopan AP | Disodiumphenyldibenz-imidazole tetrasulphonate | 1.0 |
| Amino methyl propanol | Amino methyl propanol | 2.0 |
| Dow Corning 949 cationic emulsion | Amodimethicone, cetrimonium chloride, trideceth-12 | 2.0 |
| Perfume oil PO1, PO2, PO3, PO4, or PO5 | Fragrance | 0.8 |
| 1,2-Hexa nediol | 1,2-Hexanediol | 0.5 |

TABLE 42-continued

Hair conditioner with UV protection

| Ingredients | INCI | Amount |
|---|---|---|
| 3-Hydroxypropyl caprylate | Hydroxypropyl caprylate | 0.2 |
| 3-Hydroxypropyl undecylenate | Hydroxypropyl undecylenate | 0.1 |
| Water | Water (Aqua) | ad 100 |

TABLE 43

Hair conditioner, leave on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.05 |
| Dehyguart A CA | Cetrimonium Chloride | 0.2 |
| Dehyguart SP | Quaternium-52 | 2.0 |
| Dracorin ® CE | Glyceryl Stearate Citrate | 1.0 |
| Drago-Calm | Water, Glycerin, *Avena Sativa* (Oat) Kernel Extract | 2.0 |
| Farnesol | Farnesol | |
| Perfume oil PO1, PO2, PO3, PO4, or PO5 | Fragrance | 0.5 |
| Lara Care A-200 | Galactoarabinan | 0.1 |
| Polymer JR 400 | Polyguaternium-10 | 0.1 |
| Propylene Glycol | Propylene Glycol | 0.8 |
| SymMollient ® WS | Trideceth-9, PEG-5 Isononanoate, Water | 1.0 |
| SymSol ® PF3* | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| SymTriol ® | Caprylyl Glycol, 1,2-Hexanediol, Methylbenzyl Alcohol | 1.0 |
| Water (demineralized) | Water (Aqua) | ad 100 |

TABLE 44

Anti-itch hair conditioner, leave on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| (−)-alpha Bisabolol | Bisabolol | 0.1 |
| Dehyquart A CA | Cetrimonium Chloride | 0.5 |
| Dehyquart SP | Quaternium-52 | 4.0 |
| Dracorin ® CE* | Glyceryl Stearate Citrate | 1.0 |
| Drago-Oat-Active* | Water (Aqua), Butylene Glycol, *Avena Sativa* (Oat) Kernel Extract | 2.0 |
| Perfume oil PO1, PO2, PO3, PO4, or PO5 | Fragrance | 0.1 |
| Lara Care A-200 | Galactoarabinan | 1.5 |
| Neutral Oil | Caprylic/Capric Triglyceride | 1.0 |
| PCL Liquid 100* | Cetearyl Ethylhexoate | 0.3 |
| Polymer JR 400 | Polyquaternium-10 | 0.1 |
| Propylene Glycol | Propylene Glycol | 0.8 |
| SymGlucan ® | Aqua, Glycerin, 1,2-Hexandiol, Caprylyl Glycol, Beta-Glucan | 5 |
| SymMollient ® W/S | Trideceth-9, PEG-5 Isononanoate, Water (Aqua) | 2.0 |
| SymOcide ® PH | Phenoxyethanol, Hydroxyacetophenone, Caprylyl Glycol, Aqua | 1.2 |

TABLE 44-continued

Anti-itch hair conditioner, leave on

| Ingredients | INCI | Amount |
|---|---|---|
| SymSol ® PF3* | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| Water, demineralized | Water (Aqua) | ad 100 |

TABLE 45

Sprayable hair conditioner with zinc pyrithrione, leave-on

| Ingredients | INCI | Amount |
|---|---|---|
| Monomuls 60-35 C | Hydrogenated Palm Glycerides | 1.7 |
| Cetiol OE | Dicaprylyl Ether | 7.2 |
| Abil 100 | Dimethicone | 3.6 |
| Dehyquart F 75 | Distearoylethyl Hydroxyethylmonium, Methosulfate, Cetearyl Alcohol | 4.0 |
| Eumulgin B1 | Ceteareth-12 | 3.5 |
| Cetiol S | Diethylhexylcyclohe xane | 7.2 |
| D-Panthenol | Panthenol | 0.1 |
| Glycerol 99, 5 P. | Glycerol | 1.5 |
| Water | Water (Aqua) | ad 100 |
| Actipone ® Rosemary | Water (Aqua), Propylene, Glycol, Rosmarinus Officinalis, (Rosemary) Leaf Extract | 0.1 |
| Frescolat ® ML Cryst. | Menthyl Lactate | 0.5 |
| Dragosantol100 | Bisabolol | 0.1 |
| Zinc Omadine | Zinc pyrithione | 0.1 |
| Perfume oil PO1, PO2, PO3, PO4, or PO5 | Fragrance | 0.4 |
| 2-Phenoxyethyl alcohol | Phenoxyethanol | 0.4 |
| SymSave H | Hydroxyacetophenone | 0.3 |
| SymDiol 68 | 1,2-Hexanediol, Caprylyl glycol | 0.3 |
| 3-Hydroxypropyl caprylate | Hydroxypropyl caprylate | 0.4 |
| 3-Hydroxypropyl undecylenate | Hydroxypropyl undecylenate | 0.1 |

TABLE 46

Hair styling gel

| Ingredients | Amount |
|---|---|
| Water | ad 100 |
| PVM/MA Decadiene Crosspolymer | 0.6 |
| PVP | 3.0 |
| Isocetyl Stearate | 4.0 |
| Ethylhexyl Methoxycimamate | 0.5 |
| Aminomethyl Propanol | 0.4 |
| Perfume oil PO1, PO2, PO3, PO4, or PO5 | 0.6 |
| SymDiol ® 68T (1,2-Hexanediol, 1,2-Octanediol, Tropolone) | 0.4 |
| Phenoxyethanol | 0.3 |
| 3-Hydroxypropyl caprylate | 0.2 |
| 3-Hydroxypropyl undecylenate | 0.1 |

TABLE 47

Deodorant stick

| Ingredients | Amount |
|---|---|
| Sodium stearate | 8.0 |
| PPG-3 Myristyl ether | 70.0 |
| 1,2-propylene glycol | 10.0 |
| 1,1-dimethyl-3-phenylpropanol | 0.2 |
| 2-butyloctanoic acid | 0.2 |

TABLE 47-continued

Deodorant stick

| Ingredients | Amount |
|---|---|
| Perfume oil PO1, PO2, PO3, PO4, or PO5 | 0.6 |
| Water | ad 100 |
| SymDeo Plus (Jasmol (2-benzlheptanol), 1-Dodecanol (Lauryl Alcohol), 1,2-Decanediol (Decylene Glycol), 2-Phenoxyethyl Alcohol (Phenoxyethanol)) | 0.5 |
| 3-Hydroxypropyl caprylate | 0.15 |
| Glyceryl monocaprylate | 0.15 |
| 3-Hydroxypropyl undecylenate | 0.1 |

TABLE 48

Zirconium suspensoid antiperspirant stick

| Ingredients | INCI | Amount |
|---|---|---|
| PCL Liquid 100 | Cetearyl ethylhexanonate | ad 100 |
| Silicone Fluid 345 | Cyclomethicone | 10.0 |
| CRODACOL C90 | Cetyl Alcohol | 8.0 |
| SYNCROWAX HGLC | C18-36 Triglyceride | 8.0 |
| CRODAMOL PTC | Pentaerythritol Tetracaprylate/Caprate | 5.0 |
| SYNCROWAX HRC | Tribehenin | 4.0 |
| VOLPO N5 | Oleth-5 | 1.0 |
| Titanium Dioxide | | 1.0 |
| Rezal 36GP | Aluminium Tetrachlorohydrex GLY | 20.0 |
| Dry Flo C | Aluminium Starch Octenyl Succinate | 22.5 |
| Preservative | Phenoxyethanol | 0.8 |
| Perfume oil PO1, PO2, PO3, PO4, or PO5 | Fragrance | 0.6 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |

TABLE 49

Antiperspirant/deodorant roll-on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Dragosantol ® 100* | Bisabolol | 0.1 |
| Ethanol 96% | Ethanol | 30.0 |
| Farnesol | Farnesol | 0.5 |
| Perfume oil PO1, PO2, PO3, PO4, or PO5 | Fragrance | 1.5 |
| Frescolat ®ML cryst. | Menthyl Lactate | 0.2 |
| lrgasan DP 300 | Triclosan | 0.3 |
| Natrosol 250 HHR | Hydroxyethyl-cellulose | 0.3 |
| Solubilizer 611674 | PEG-40 Hydrogenated Castor Oil, Trideceth-9, Water (Aqua) | 2.0 |
| SymDeo ® B125 | 2-Methyl 5-Cyclohexylpentanol | 0.5 |
| Water (demineralized) | Water (Aqua) | ad 100 |
| Zirkonal L 450 | Aluminium Zirconium Pentachloro-hydrate (40% aqueous solution) | 37.0 |

TABLE 50

| Deodorant formulation in the form of a roll-on gel | |
| --- | --- |
| Ingredients | Amount |
| 1,3-butylene glycol | 2.0 |
| PEG-40-hydrogenated castor oil | 2.0 |
| Hydroxyethylcellulose | 0.5 |
| Perfume oil PO1, PO2, PO3, PO4, or PO5 | 0.3 |
| 1,3-propanediol | 0.5 |
| SymGuard CD (3-Phenylpropanol, o-cymen-3-ol, Decylene glycol) | 0.4 |
| Ethylhexyl glycerin | 0.1 |
| 3-Hydroxypropyl caprylate | 0.3 |
| Glyceryl monocaprylate | 0.15 |
| 3-Hydroxypropyl undecylenate | 0.1 |
| Water | ad 100 |

TABLE 51

| Clear deo anti-perspirant roll-on | | |
| --- | --- | --- |
| Ingredients | INCI | Amount |
| Methocel E4M Premium | Hydroxypropyl Methylcellulose | 0.5 |
| Water | Water (Aqua) | ad 100 |
| Neo-PCL Water Soluble N | Trideceth-9, PEG-5 Ethylhexanoate, Water (Aqua) | 1.0 |
| Solubilizer | PEG-40 Hydrogenated Castor Oil, Trideceth-9, Propylene Glycol, Water (Aqua) | 3.0 |
| Deolite | Dimethyl Phenylpropanol, Pentylene Glycol | 0.5 |
| Locron LW | Aluminium Chlorohydrate | 25.0 |
| Aloe Vera Gel Concentrate 10/1 | Aloe Barbadensis Leaf Juice | 1.0 |
| 1,2-Propylene Glycol 99 P GC | Propylene Glycol | 4.0 |
| Ethanol 96% | Alcohol Denat. | 30.0 |
| Perfume oil PO1, PO2, PO3, PO4, or PO5 | Fragrance | 1.0 |
| 3-Hydroxypropyl caprylate | Hydroxypropyl caprylate | 0.3 |
| 3-Hydroxypropyl undecylenate | Hydroxypropyl undecylenate | 0.15 |

TABLE 52

| Deodorant pump spray with SymClariol | | |
| --- | --- | --- |
| Ingredients | INCI | Amount |
| SymClariol ® | Decylene Glycol | 0.2 |
| Solubilizer | PEG-40 Hydrogenated Castor Oil, Trideceth-9, Propylene Glycol, Water (Aqua) | 4.0 |
| Neo-PCL Water Soluble N | Trideceth-9, PEG-5 Ethylhexanoate, Aqua | 1.5 |
| SymRelief ® | Bisabolol, Zingiber Officinale (Ginger) Root Extract | 0.1 |
| Water | Water (Aqua) | ad 100 |
| 1,2-Propylene Glycol | Propylene Glycol | 6.0 |
| Perfume oil PO1, PO2, PO3, PO4, or PO5 | Perfume | 0.4 |
| SymDiol ® 68 | 1,2-Hexanediol, Caprylyl Glycol | 0.2 |
| 3-Hydroxypropyl caprylate | Hydroxypropyl caprylate | 0.2 |
| 3-Hydroxypropyl undecylenate | Hydroxypropyl undecylenate | 0.1 |

TABLE 53

| Deodorant spray | |
| --- | --- |
| Ingredients | Amount |
| PEG-40-hydrogenated castor oil | 3.0 |
| Ethylhexylglycerol (Octoxyglycerol) | 0.2 |
| Ethanol | 40.0 |
| Citrate buffer | 0.5 |
| 1,2-Hexanediol, 1,2-Octanediol (1:1) | 0.3 |
| SymOcide C (o-cymen-5-ol) | 0.05 |
| 2-Benzylheptan-1-ol (Jasmol) | 0.1 |
| Perfume oil PO1, PO2, PO3, PO4, or PO5 | 0.75 |
| Phenoxyethanol | 0.4 |
| 3-Hydroxypropyl caprylate | 0.2 |
| Glyceryl monoundecylenate | 0.1 |
| Water | ad 100 |

TABLE 54

| Sunscreen lotion (o/w, broadband protection) | | |
| --- | --- | --- |
| Ingredients | INCI | Amount |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |
| Carbopol Ultrez-10 | Carbomer | 0.2 |
| Dow Corning 246 Fluid | Cyclohexasiloxane and Cyclopentasiloxane | 2.0 |
| Dragosantol ® 100* | Bisabolol | 0.3 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.4 |
| Frescolat ®MGA | Menthone Glycerol Acetal | 0.3 |
| Glycerol 85% | Glycerin | 4.7 |
| Keltrol RD | Xanthan Gum | 0.2 |
| Lanette O | Cetearyl Alcohol | 1.0 |
| Neo Heliopan ® 357 | Butyl Methoxy-dibenzoyl-methane | 1.0 |
| Neo Heliopan ® AP (10% as sodium salt) | Disodium Phenyl Dibenzimidazole Tetrasulfonate | 10.0 |
| Neo Heliopan ® AV | Ethylhexyl Methoxy-cinnamate | 3.0 |
| Neo Heliopan ® Hydro (15% as sodium salt) | Phenylbenz-imidazole Sulfonic Acid | 6.7 |
| Neo Heliopan ® MBC | 4-Methylbenzyl-idene Camphor | 1.5 |
| Neo Heliopan ® OS | Ethylhexyl Salicylate | 5.0 |
| Neutral Oil | Caprylic/Capric Triglyceride | 2.0 |
| SymMatrix ® | Maltodextrin, Rubus Fruticosus (Blackberry) Leaf Extract | 0.3 |
| SymOcide ® BHO | Hydroxyacetophenone, Benzyl alcohol, Caprylyl glycol, Aqua | |
| Tegosoft TN | C12-15 Alkyl Benzoate | 5.0 |
| Tocopherol Acetate | Tocopheryl Acetate | 0.5 |
| Triethanolamine, 99% | Triethanolamine | 0.5 |
| Water (demineralized) | Water (Aqua) | ad 100 |

TABLE 55

| Emulsion with UV-A/B-broadband protection | | |
| --- | --- | --- |
| Ingredients | INCI | Amount |
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.3 |
| Butylene Glycol | Butylene Glycol | 3.0 |
| Carbopol Ultrez-10 | Carbomer | 0.2 |
| Citric Acid 10% sol. | Citric Acid | 0.3 |

TABLE 55-continued

Emulsion with UV-A/B-broadband protection

| Ingredients | INCI | Amount |
|---|---|---|
| Dragosantol ® 100* | Bisabolol | 0.1 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.1 |
| Frescolat ®X-COOL | Menthyl Ethylamido Oxalate | 1.0 |
| Glyceryl Stearate | Glyceryl Stearate | 2.0 |
| Keltrol RD | Xanthan Gum | 0.2 |
| Lanette 16 | Cetyl Alcohol | 1.2 |
| Lanette E | Sodium Cetearyl Sulfate | 0.7 |
| Neo Heliopan ® AP (10% as sodium salt) | Disodium Phenyl Dibenzimidazole Tetrasulfonate | 22.0 |
| Neo Heliopan ® HMS | Homosalate | 5.0 |
| Neutral Oil | Caprylic/Capric Triglyceride | 2.0 |
| PCL Liquid 100 | Cetearyl Ethylhexoate | 3.0 |
| Sodium Hydroxide (10% sol.) | Sodium Hydroxide | 2.8 |
| Symdiol ®68 | 1,2-Hexanediol, Caprylylglycol | 0.5 |
| SymMollient ®S | Cetearyl Nonanoate | 1.5 |
| SymSitive ® 1609 | Pentylene Glycol, 4-t-Butylcyclohexanol | 0.5 |
| SymWhite ®377 | Phenylethyl Resorcinol | 0.5 |
| Tocopherol Acetate | Tocopheryl Acetate | 0.5 |
| Water (demineralized) | Water (Aqua) | ad 100 |

TABLE 56

Sun protection soft cream (w/o), SPF 40

| Ingredients | INCI | Amount |
|---|---|---|
| Dehymuls PGPH | Polyglyceryl-2 dipolyhydroxystearate | 5.0 |
| Copherol 1250 | Tocopheryl acetate | 0.5 |
| Permulgin 3220 | Ozocerite | 0.5 |
| Zinc stearate | Zinc stearate | 0.5 |
| Tegosoft TN | C12-15 Alkyl benzoate | 10.0 |
| Neo Heliopan ® E1000 | Isoamyl-p-methoxycinnamate | 2.0 |
| Neo Heliopan ® 303 | Octocrylene | 5.0 |
| Neo Heliopan ® MBC | 4-Methylbenzylidene camphor | 3.0 |
| Zinc oxide, neutral | Zinc oxide | 5.0 |
| Water, distilled | Water (aqua) | ad 100 |
| EDETA BD | Disodium EDTA | 0.1 |
| Glycerol | Glycerol | 4.0 |
| Magnesium sulfate | Magnesium sulfate | 0.5 |
| Perfume oil PO1, PO2, PO3, PO4, or PO5 | Fragrance | 0.3 |
| Symdiol ® 68 | 1,2-Hexanediol, Caprylylglycol | 0.3 |
| 3-Hydroxypropyl caprylate | Hydroxypropyl caprylate | 0.15 |
| Glyceryl monocaprylate | Glyceryl caprylate | 0.15 |

TABLE 57

Sun protection milk (w/o)

| Ingredients | INCI | Amount |
|---|---|---|
| Dehymuls PGPH | Polyglyceryl-2 dipolyhydroxystearate | 3.0 |
| Beeswax 8100 | Beeswax | 1.0 |
| Monomuls 90-0-18 | Glyceryl oleate | 1.0 |
| Zinc stea rate | Zinc stearate | 1.0 |
| Cetiol SN | Cetearyl isononanoate | 5.0 |
| Cetiol OE | Dicaprylyl ether | 5.0 |
| Tegosoft TN | C12-15 alkyl benzoate | 4.0 |
| Vitamin E | Tocopherol | 0.5 |
| Neo Heliopan ® OS | Ethylhexyl salicylate | 5.0 |
| Neo Heliopan ® AV | Ethylhexyl methoxycinnamate | 7.5 |
| Uvinul ® T150 | Ethylhexyl triazone | 1.5 |
| Water, distilled | Water (Aqua) | ad 100 |

TABLE 57-continued

Sun protection milk (w/o)

| Ingredients | INCI | Amount |
|---|---|---|
| Trilon BD | Disodium EDTA | 0.1 |
| Glycerol | Glycerol | 5.0 |
| Neo Heliopan ® AP 10% solution, neutralized with NaOH | Disodium phenyl dibenzimidazole tetrasulfonate | 15.0 |
| Perfume oil PO1, PO2, PO3, PO4, or PO5 | Fragrance | 0.25 |
| Alpha bisabolol | Bisabolol | 0.1 |
| SymOcide ® PT | Phenoxyethanol, Tropolone | 0.25 |
| 3-Hydroxypropyl caprylate | Hydroxypropyl caprylate | 0.2 |
| 3-Hydroxypropyl undecylenate | Hydroxypropyl undecylenate | 0.1 |

TABLE 58

Sun spray with UV-A/B-broadband protection with low oil content

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| Ethanol 96% | Ethanol | 13.0 |
| Perfume oil PO1, PO2, PO3, PO4, or PO5 | Fragrance | 0.5 |
| Glyceryl Stearate | Glyceryl Stearate | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Isoadipate ® | Diisopropyl Adipate | 1.0 |
| Neo Heliopan ® AV | Ethylhexyl Methoxy-cinnamate | 25.0 |
| Neo Heliopan ® MBC | 4-Methylbenzyl-idene Camphor | 33.3 |
| Propylene Glycol | Propylene Glycol | 0.8 |
| Tego Betain L7 | Cocamidopropyl Betaine | 1.0 |
| Water (demineralized) | Water (Aqua) | ad 100 |

TABLE 59

Sunscreen spray o/w, SPE 15-20

| Ingredients | INCI | Amount |
|---|---|---|
| Dracorin ® GOC | Glyceryl Oleate Citrate, Caprylic/Capric Triglyceride | 2.0 |
| Corapan ® TQ | Diethylhexyl 2,6-Naphthalate | 3.0 |
| Neo Heliopan ® HMS | Homosalate | 7.0 |
| Neo Heliopan ® OS | Ethylhexyl Salicylate | 5.0 |
| Neo Heliopan ® 357 | Butyl Methoxydibenzoylmethane | 3.0 |
| Isoadipate | Diisopropyl Adipate | 6.0 |
| Baysilone ® Oil M10 | Dimethicone | 1.0 |
| Edeta ® BD | Disodium EDTA | 0.1 |
| Vitamin E Acetate | Tocopheryl Acetate | 0.5 |
| Dragosantol ® 100 | Bisabolol | 0.1 |
| Pemulen ® TR-2 | Acrylates/C10-30 Alkyl Acrylate Crosspolymer | 0.25 |
| Water | Water (Aqua) | ad 100 |
| Glycerol 99, 5 P. | Glycerol | 4.0 |
| Butylene Glycol | Butylene Glycol | 5.0 |
| Neo Heliopan ® Hydro (103089), used as 25% aq. solution neutralized with Biotive ® L-Arginine | Phenylbenzimidazole Sulfonic Acid | 8.0 |
| Biotive ® L-Arginine | Arginine | 0.55 |
| Perfume oil PO1, PO2, PO3, PO4, or PO5 | Fragrance | 0.4 |

45

TABLE 59-continued

Sunscreen spray o/w, SPE 15-20

| Ingredients | INCI | Amount |
|---|---|---|
| SymOcide PS | Phenoxyethanol, 1,2-Hexanediol, Decylene glycol | 0.8 |
| Glyceryl monocaprylate | Glyceryl caprylate | 0.2 |
| 3-Hydroxypropyl undecylenate | Hydroxypropyl undecylenate | 0.1 |

TABLE 60

After sun gel

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.0 |
| Glycerol 99, 5 P. | Glycerol | 5.0 |
| SymHelios ® 1031 | Benzylidene Dimethoxydimethylin danone | 0.1 |
| Water | Water (Aqua) | ad 100 |
| Pemulen ® TR-2 | Acrylates/C10-30 Alkyl Acrylate Crosspolymer | 1.0 |
| D-Panthenol 75 W | Panthenol | 0.5 |
| SymFinity ® 1298 | *Echinacea Purpurea* Extract | 0.1 |
| Extrapone ® Pearl GW | Water (Aqua), Glycerol, Hydrolyzed Pearl, Xanthan Gum | 1.0 |
| Sodium Hydroxide 10% solution | Sodium Hydroxide | 2.5 |
| Ethanol 96% | Alcohol Denat. | 15.0 |
| Perfume oil PO1, PO2, PO3, PO4, or PO5 | Fragrance | 0.2 |
| SymOcide ® PS | Phenoxyethanol, 1,2-Hexanediol, Decyleneglycol | 0.8 |
| 3-Hydroxypropyl caprylate | Hydroxypropyl caprylate | 0.15 |
| 3-Hydroxypropyl undecylenate | Hydroxypropyl undecylenate | 0.05 |

TABLE 61

After sun lotion

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil PO1, PO2, PO3, PO4, or PO5 | 0.30 |
| 1,2-Hexanediol | 1.0 |
| 4-Hydroxyacetophenone | 0.3 |
| Pentylene glycol | 4.0 |
| Aqua dem. | ad 100 |
| Triethanolamine | 0.2 |
| 3-Hydroxypropyl caprylate | 0.2 |
| 3-Hydroxypropyl undecylenate | 0.1 |

TABLE 62

Syndet antimicrobial soap bar

| Ingredients | INCI | Amount |
|---|---|---|
| Zetesap 813 A | Disodium Lauryl Sulfosuccinate, Sodium Lauryl Sulfate, Corn Starch, | ad 100 |

46

TABLE 62-continued

Syndet antimicrobial soap bar

| Ingredients | INCI | Amount |
|---|---|---|
|  | Cetearyl Alcohol, Paraffin, Titanium Dioxide | |
| Amphotensid GB 2009 | Disodium Cocoamphodiacetate | 6.0 |
| Allantoin | Allantoin | 1.0 |
| Perfume oil PO1, PO2, PO3, PO4, or PO5 | Fragrance | 1.0 |
| SymOcide C | o-cymen-5-ol | 0.1 |
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |

TABLE 63

Syndet soap bar

| Ingredients | INCI | Amount |
|---|---|---|
| Fenopon AC-78 | Sodium Cocoyl Isethionate | 20.0 |
| Natriumlaurylsulfoacetate | Sodium Lauryl Sulfoacetate | 16.0 |
| Paraffin | Paraffin | 19.0 |
| Wax, microcrystalline | Microcrystalline Wax | 1.0 |
| Corn Starch | Corn Starch | 8.0 |
| Coconut acid | Coconut acid | 2.0 |
| Lauric acid diethanol amide | Lauramide DEA | 2.0 |
| Dextrin | Dextrin | 21.0 |
| Lactic acid, 88% | Lactic Acid | 1.0 |
| SymGuard CD | 3-Phenylpropanol, o-cymen-5-ol, Decylene glycol | 0.3 |
| Thymol | Thymol | 0.05 |
| Water | Water | ad 100 |
| Perfume oil PO1, PO2, PO3, PO4, or PO5 | Fragrance | 1.0 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 64

Antimicrobial toilet soap bar

| Ingredients | Amount |
|---|---|
| Sodium soap from tallow | 60.0 |
| Sodium soap from palm oil | 27.0 |
| Glycerol | 2.0 |
| Sodium Chloride | 0.5 |
| 1-Hydroxyethane-1,1-diphosphonic acid, tetrasodium salt | 0.3 |
| Alpha-Tocopherol | 0.1 |
| Pigment Yellow 1 | 0.02 |
| Water | ad 100 |
| Perfume oil PO1, PO2, PO3, PO4, or PO5 | 3.0 |
| Farnesol | 0.2 |
| 3-Hydroxypropyl caprylate | 0.1 |
| Glyceryl monocaprylate | 0.1 |
| 3-Hydroxypropyl undecylenate | 0.05 |
| Glyceryl monoundecylenate | 0.05 |

TABLE 65

Shaving foam

| Ingredients | Amount |
| --- | --- |
| Dem. Water | ad 100 |
| Triethanolamine | 4.0 |
| Edenor L2 SM (Stearinic acid, Palmitinic acid) (Cognis) | 5.3 |
| Laureth-23 | 3.0 |
| Stearylalcohol | 0.5 |
| SymOcide BHO | 1.0 |
| (Hydroxacetophenone, Benzyl alcohol, | |
| Caprylyl glycol, Water) | |
| 3-Hydroxypropyl caprylate | 0.2 |
| Glyceryl monocaprylate | 0.1 |
| 3-Hydroxypropyl undecylenate | 0.1 |
| Glyceryl monoundecylenate | 0.05 |
| Sodium lauryl sulfate | 3.0 |
| Extrapone Seaweed (water, propylene glycol, | 1.0 |
| potassium iodide, *Fucus Vesiculosus* Extract) | |
| Dragosantol (Bisabolol, Farnesol) | 0.1 |
| Perfume oil PO1, PO2, PO3, PO4, or PO5 | 1.0 |
| propane, butane 4, 2 Bar | 4.0 |

TABLE 66

Sprayable disinfecting gel

| Ingredients | INCI | Amount |
| --- | --- | --- |
| Water | Water (Aqua) | ad 100 |
| Stabileze QM | PVM/Ma Decadiene Crosspolymer | 0.25 |
| Sodium Hydroxide 10% solution | Sodium Hydroxide | 0.4 |
| Coffein pure | Caffeine | 0.5 |
| Extrapone ® Horse Chestnut | Propylene Glycol, Water (Aqua), Glucose, *Aesculus Hippocastanum* (Horse Chestnut) Seed Extract, Lactic Acid | 1.0 |
| Hydrolite ® 5 | Pentylene Glycol | 3.0 |
| 1,3 Butylene Glycol | Butylene Glycol | 5.0 |
| Biotive ® Esculin Sesquihydrate | Esculin | 0.3 |
| Ethanol 96% | Alcohol Denat. | 10.0 |
| Solubilizer | PEG-40 Hydrogenated Castor Oil, Trideceth-9, Water (Aqua) | 0.5 |
| Perfume oil PO1, PO2, PO3, PO4, or PO5 | Fragrance | 0.2 |
| Octenidine dihydrochloride | | 0.1 |
| Preservative | Phenoxyethanol | 0.7 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 67

Solution for wet wipes

| Ingredients | INCI | Amount |
| --- | --- | --- |
| SymSol ® PF-3 | Water (Aqua), Pentylene Glycol, Sodium Lauryl Sulfoacetate, SodiumOleoyl Sarcosinate, Sodium Chloride, Disodium Sulfoacetate, SodiumOleate, Sodium Sulfate | 2.0 |
| Dragosantol ® 100 | Bisabolol | 0.1 |
| Glycerol 99, 5 P. | Glycerol | 5.0 |
| Water | Water (Aqua) | ad 100 |
| Hydrolite ® 5 | Pentylene Glycol | 5.0 |
| D-Panthenol 75 W | Panthenol | 0.8 |
| DragoCalm ® | Water (Aqua), Glycerol, *Avena Sativa* (Oat) Kernel Extract | 1.0 |
| Witch Hazel-Distillate | *Hamamelis Virginiana* (Witch Hazel) Water, Water (Aqua), Alcohol | 1.0 |

TABLE 67-continued

Solution for wet wipes

| Ingredients | INCI | Amount |
| --- | --- | --- |
| Allplant Essence ® Org. Rose *Geranium P* | *Pelargonium Graveolens* Flower/Leaf/Stem Water | 1.0 |
| Perfume oil PO1, PO2, PO3, PO4, or PO5 | Fragrance | 0.1 |
| SymOcide BHO | Benzyl alcohol, Hydroxyacetophenone, Caprylyl glycol, Water | 0.8 |
| 3-Hydroxypropyl caprylate | Hydroxypropyl caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |

6.) In Vivo Study

An in vivo study was performed to investigate the potential of 3-hydroxypropyl caprylate for scalp care. The study groups contained 22 persons for the product with active ingredient (3-hydroxypropyl caprylate) and 12 persons for the placebo. The efficacy was assessed based on dermatological evaluation regarding itching as well as on individual subjective perception (questionnaire).

The active ingredient was provided in a leave-on pump spray (formulation of 0.5 wt.-% of 3-hydroxypropyl caprylate in ethanol/water 70/30 vol/vol; ethanol/water 70/30 vol/vol as placebo). After two weeks of wash out with an active free shampoo, the test product was applied once daily to the scalp (30 spray bursts, every evening, leave-on overnight) for four weeks, while washing with the active free shampoo continued as during the first two weeks of wash out.

The dermatological evaluation was performed after the two weeks of wash out with active free shampoo by a trained technician on day 1 (before first use of the active-containing leave on-pump spray) and after 28 days of product application (evaluation at day 29). The intensity of itching was determined on a relative scale with the following scores: 0=none; 0.5=very slight; 1=slight; 2=moderate; 3=strong.

Figure 5:
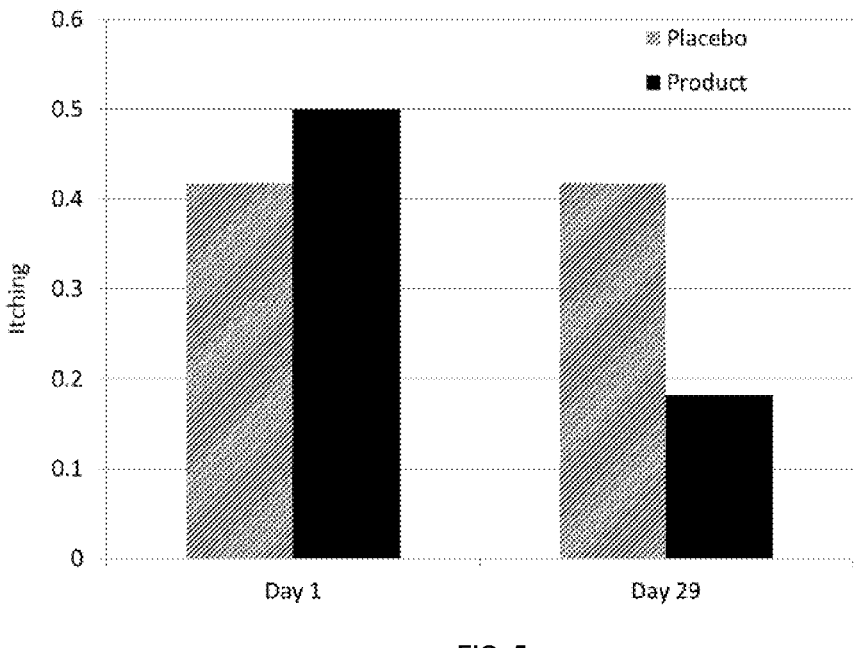
FIG. 5 illustrates the reduction in scalp itching intensity observed in an in vivo study comparing a leave-on pump spray containing 3-hydroxypropyl caprylate to a placebo after four weeks of daily use.

FIG. 5 shows significant reduction of itching in dermatological evaluation in the in vivo study with 22 participants (product with 3-hydroxypropyl caprylate) and 12 participants (placebo) after 4 weeks of application as described above.

The questionnaire with the following questions was answered by each participant on day 29 of the treatment with the leave-on pump spray (as described above):

Question 1 (Q1): After test product application: The scalp feels well-cared.

Question 2 (Q2): After the application, the scalp feeling is pleasant.

Question 3 (Q3): The product is effective against itching.

The acceptance was determined on a relative scale with the following scores: −2=fully disagree; −1=rather disagree; 0=neither . . . nor; 1=rather agree; 2=fully agree.

Figure 6:
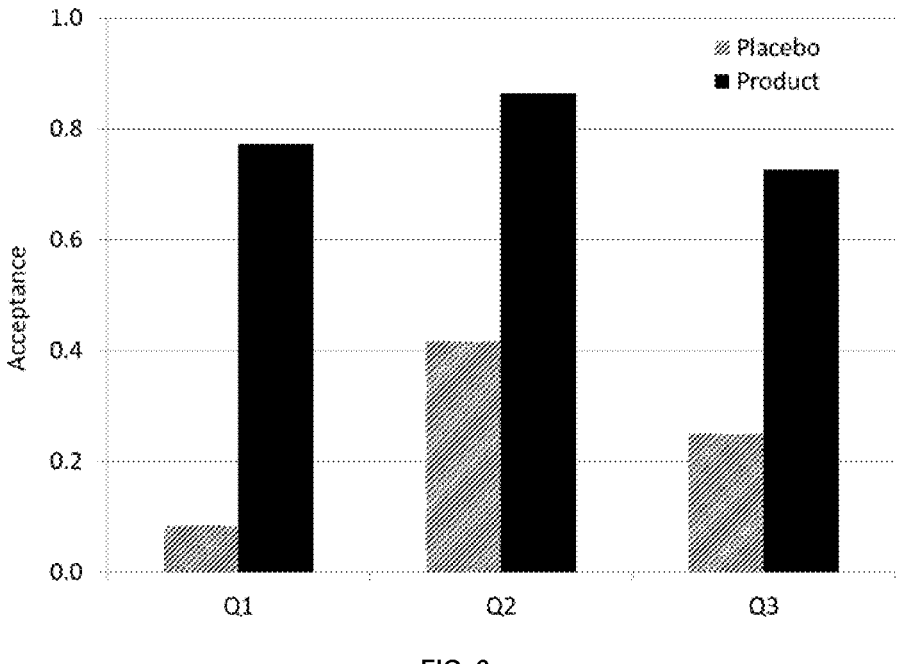
FIG. 6. presents the acceptance results from the same in vivo study, showing participant ratings regarding scalp care sensation, pleasantness of feel, and perceived anti- itch efficacy of the product containing 3-hydroxypropyl caprylate.

FIG. 6 shows the acceptance of the product in the in vivo study based on the answers provided by the participants of the study.

The invention claimed is:

1. A skin or hair care product comprising:
(a) an amount of 0.3 to 5 wt. %, based on the total weight of the skin or hair care product, of one or more fatty acid esters, provided the amount enhances foam formation of the product and/or improves a sensation of smoothness, moisturization, and/or re-fattening to skin upon application of the product to the skin, wherein the one or more fatty acid esters are chosen from 3-hydroxypropyl caprylate and 3-hydroxypropyl undecylenate; and (b) (i) one or more surfactants chosen from sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol distearate, and sodium oleoyl sarcosinate; and/or (ii) one or more emulsifiers chosen from PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer, ammonium acryloyldimethyltaurate/beheneth-25 methacrylate crosspolymer, polyglyceryl-4 caprate, polyglyceryl-4 caprylate/caprate, cetyl PEG/PPG-10/1, dimethicone, polyglycer-yl-6 dioleate, polyglyceryl -2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate, polyglyceryl-3 dicitrate/stearate, and PEG-40 hydrogenated castor oil.

2. The product according to claim 1, wherein the one or more fatty acid esters are in an amount sufficient to prevent and/or reduce dandruff.

3. A method for modifying sensory properties of a skin or hair care product comprising:

(i) providing ingredients of a skin or hair care product, wherein the ingredients comprise:

(a) one or more surfactants chosen from sodium lauryl ether sulfate cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol distearate, and sodium oleoyl sarcosinate, and/or (b) one or more emulsifiers chosen from PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer, ammonium acryloyldimethyltaurate/beheneth-25 methacrylate crosspolymer, polyglyceryl-4 caprate, polyglyceryl-4 caprylate/caprate, cetyl PEG/PPG-10/1, dimethicone, polyglycer-yl-6 dioleate, polyglyceryl -2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate, polyglyceryl-3 dicitrate/stearate, and PEG-40 hydrogenated castor oil;

(ii) incorporating an amount of 0.3 to 5 wt. %, based on the total weight of the skin or hair care product, of one or more fatty acid esters, provided the amount enhances foam formation of the product and/or improves a sensation of smoothness, moisturization, and/or re-fattening to skin upon application of the product to the skin, wherein the one or more fatty acid esters are chosen from 3-hydroxypropyl caprylate and 3-hydroxypropyl undecylenate, and (iii) mixing the components of (i) and (ii).

4. The method according to claim 3, wherein the product is a leave-on product or a rinse-off product.

5. The method according to claim 3, wherein the product is a shampoo and the amount of the one or more fatty esters is such that the resulting product is an anti-dandruff shampoo.

6. A method for manufacturing a skin or hair care product comprising:

(i) providing ingredients of a skin or hair care product, wherein the ingredients comprise:

(a) one or more surfactants chosen from sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol distearate, and sodium oleoyl sarcosinate, and/or (b) one or more emulsifiers chosen from PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer, ammonium acryloyldimethyltaurate/beheneth-25 methacrylate crosspolymer, polyglyceryl-4 caprate, polyglyceryl-4 caprylate/caprate, cetyl PEG/PPG-10/1, dimethicone, polyglycer-yl-6 dioleate, polyglyceryl -2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate, polyglyceryl-3 dicitrate/stearate, and PEG-40 hydrogenated castor oil;

(ii) providing an amount of 0.3 to 5 wt. %, based on the total weight of the skin or hair care product, of one or more fatty acid esters, provided the amount enhances foam formation of the product and/or improves a sensation of smoothness, moisturization, and/or re-fattening to skin upon application of the product to the skin, wherein the one or more fatty acid esters are chosen from 3-hydroxypropyl caprylate and 3-hydroxypropyl undecylenate, and (iii) mixing the components of (i) and (ii).

7. The method according to claim 6, wherein the product is a shampoo and the amount of the one or more fatty esters is such that the resulting product is an anti-dandruff shampoo.

8. The product according to claim 1, wherein the product is a shampoo comprising:

(i) water, (ii) one or more surfactant(s) chosen from sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, coc-amide-MEA, PEG-7 glyceryl cocoate, glycol distearate, and sodium oleoyl sarcosinate, (iii) one or more fatty acid esters chosen from 3-hydroxypropyl caprylate and 3-hydroxypropyl undecylenate, (iv) one or more fragrance(s), (v) optionally, one or more plant oil(s) chosen from persea gratissima oil, olea europaea oil, prunus amygdalus dulcis oil, helianthus annuus seed oil, simmondsia chinensis seed oil, mauritia flexuosa fruit oil, calophyllum inophyllum seed oil, and triticum vulgare germ oil, (vi) optionally, one or more preservative(s) chosen from 2-phenoxyethanol, benzyl alcohol, dehydroacetic acid, methyl paraben, sorbic acid, and benzoic acid, and (vii) optionally, one or more active ingredient(s) chosen from 4-hydroxyacetophenone, 1,2-pentanediol, 1,2-hexanediol, 1,2-octanediol, 1,2-decanediol, caprylhydroxamic acid, sorbitan caprylate, ethylhexylglycerine, laureth-9, crisaborol, trideceth-9, PEG-5 isononanoate, 4-t-butylcyclohexanol, hydroxyphenyl propamidobenzoic acid, avananthramides, polyphenols from oats, hydrocortisone, and urea.

9. The product according to claim 1, wherein the product is a hair or body cream comprising:

(i) water, (ii) one or more emulsifying agent(s) chosen from PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer, ammonium acryloyldimethyltaurate/Beheneth-25 methacrylate crosspolymer, polyglyceryl-4 caprate, polyglyceryl-4 caprylate/caprate, cetyl PEG/PPG-10/1, dimethicone, polyglycer-yl-6 dioleate, polyglyceryl-2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate, polyglyceryl-3 dicitrate/stearate, and PEG-40 hydrogenated castor oil, (iii) one or more oil body/bodies chosen from caprylic capric triglycerides, mineral oil, simmondsia chinensis seed oil, butyrospermum parkii butter, dicaprylyl ether, cyclomethicone, dimethicone, C12-15 alkyl benzoate, isopropyl palmitate, isopropyl myristate, octyldodecanol, cetearyl ethylhexanoate, cetearyl nonanoate, ethylhexyl isononanoate, propylene glycol dicaprylate/dicaprate, propylheptyl caprylate, decyl oleate, hexyl laurate, ethylhexyl stearate, triisononanoin, iso-adipate, stearyl heptanoate, and stearyl caprylate, (iv) one or more fatty acid esters chosen from 3-hydroxypropyl caprylate and 3-hydroxypropyl undecylenate, (v) one or more fragrance(s), (vi) optionally, one or more preservative(s) chosen from 2-phenoxyethanol, benzyl alcohol, dehydroacetic acid, methyl paraben, sorbic acid and benzoic acid, and (vii) optionally, one or more active ingredient(s) chosen from 4-hydroxyacetophenone, 1,2-pentanediol, 1,2-hexanediol, 1,2-octanediol, 1,2-decanediol, caprylhydroxamic acid, sorbitan caprylate, ethylhexylglycerine, laureth-9, crisaborol, trideceth-9, PEG-5 isononanoate, 4-t-butylcyclohexanol, hydroxyphenyl propamidobenzoic acid, avananthramides, polyphenols from oats, hydrocortisone, and urea.

10. The product according to claim 1, wherein the product is in the form of an oil-in-water emulsion, a water-in-oil emulsion, an aqueous formulation, or an aqueous and/or ethanolic and/or glycolic-based formulation.

11. The product according to claim 1, wherein the product is a rinse-off product.

12. The product according to claim 1, wherein the product is a leave-on product.

13. The product according to claim 11, wherein the product is a cleansing product.

14. The product according to claim 13, wherein the product is a shampoo.

15. The product according to claim 14, wherein the shampoo is an anti-dandruff shampoo.

16. The product according to claim 10, wherein the product is in the form of an oil-in-water emulsion or a water-in-oil emulsion.

17. The product according to claim 1, comprising the 3-hydroxypropyl caprylate.

18. The product according to claim 1, comprising the 3-hydroxypropyl undecylenate.

* * * * *